US008114669B2

(12) United States Patent
Choo

(10) Patent No.: US 8,114,669 B2
(45) Date of Patent: Feb. 14, 2012

(54) CELL CULTURE

(75) Inventor: Yen Choo, London (GB)

(73) Assignee: Plasticell Limited, London (GB)

(*) Notice: Subject to any disclaimer, the term of this patent is extended or adjusted under 35 U.S.C. 154(b) by 913 days.

(21) Appl. No.: 10/530,128

(22) PCT Filed: Oct. 3, 2003

(86) PCT No.: PCT/GB03/04287
§ 371 (c)(1),
(2), (4) Date: Oct. 21, 2005

(87) PCT Pub. No.: WO2004/031369
PCT Pub. Date: Apr. 15, 2004

(65) Prior Publication Data
US 2007/0298411 A1    Dec. 27, 2007

(30) Foreign Application Priority Data
Oct. 3, 2002    (GB) .................................. 0222846.8

(51) Int. Cl.
*C12N 5/00* (2006.01)
*C12N 5/02* (2006.01)
*C12N 1/20* (2006.01)
*C12N 9/00* (2006.01)
*C12N 1/00* (2006.01)
*C07K 1/00* (2006.01)
*A01N 63/00* (2006.01)

(52) U.S. Cl. ...................... 435/383; 435/420; 435/252.4; 435/183; 435/325; 435/243; 435/273; 435/410; 424/93.1

(58) Field of Classification Search ........................ None
See application file for complete search history.

(56) References Cited

U.S. PATENT DOCUMENTS

| 5,811,238 | A | 9/1998 | Stemmer et al. | |
|---|---|---|---|---|
| 5,965,437 | A | 10/1999 | Scadden | |
| 6,001,585 | A | 12/1999 | Gramer | 435/29 |
| 7,041,438 | B2 | 5/2006 | Carpenter et al. | |
| 2001/0051834 | A1 | 12/2001 | Frondoza et al. | 623/23.72 |
| 2003/0036194 | A1 | 2/2003 | Xu et al. | |
| 2003/0113813 | A1 | 6/2003 | Heidaran et al. | |
| 2004/0170965 | A1* | 9/2004 | Scholl et al. | 435/5 |
| 2005/0154534 | A1 | 7/2005 | Haaland et al. | |

FOREIGN PATENT DOCUMENTS

| EP | 0695351 | 12/1999 |
|---|---|---|
| WO | WO 2004/031369 A1 | 4/2004 |

OTHER PUBLICATIONS

Nishikawa et al. (Develpoment, 1998; 125: 1747-1757).*
International Search Report from PCT/GB2003/004287 mailed on Mar. 1, 2004.
Einspanier R., et al., "First Identification of Caldesmon Transcripts in Bovine Oviduct Epithelial Cells in vitro by means of an RNA Differential Display Technique Examining Culture-induced Expression Changes," *Reprod Dorn Anim*, 2001, 36:230-235.
Freshney R. Ian, *Culture of Animal Cells, a Manual of Basic Technique, Third Edition*, 1994, pp. 161-166, Wiley-Liss Inc., New York.
Jordan F.L., et al., "Method for the Identification of Brain Macrophages/Phagocytic Cells In Vitro," *Journal of Neuroscience Research*, 1990, 26:74-82.
Mellado-Damas N., et al., "Ex-vivo expansion and maturation of CD34-positive hematopoietic progenitors optimization of culture conditions," *Leukemia Research*, 1999, 23:1035-1040.
Zimrin Ann B., et al., "Models of In Vitro Angiogenesis: Endothelial Cell Differentiation on Fibrin but not Matrigel is Transcriptionally Dependent," *Biochemical and Biophysical Research Communications*, Aug. 15, 1995, 213(2):630-638.
Vadim V Demidov,(2002) "Rolling-circle amplificationin DNA diagnostics: the power of simplicity" Expert Rev. Mol. Diagn. 2(6) pp. 542-548.
Toma et al, (2001) "Isolation of multipotent adult stem cells from the dermis of mamalian skin" Nature Cell Biology vol. 3, pp. 778-784.
Chia-Ning Shen, et al.,(2000) "Molecular basis of transdifferentiation of pancreas to liver"Nature Cell Biology vol. 2, pp. 879-887.
Horb et al., (2003) "Experimental Conversionof Liver to Pancreas" Current Biology vol. 13, pp. 105-115.
Lee et al., (2000) "Efficient generation of omidbrain and hindbrain neurons form mouse embryonic stem cells" Nature Biotechnology, vol. 19 pp. 675-679.
Bonner-Weir, et al., (2000) "In vitro cultivationof human islets from expanded ductal tissue" PNAS: vol. 97, pp. 7999-8004.
Lumelsky, et al., (2000) "Differentiation of Embryonic Stem Cells to Insulin-Secreting Structures Similar to Pancreatic Islets" Science vol. 292, pp. 1389-1394.
Nishikawa, et al., (1998) "Progressive lineage analysis by cell sorting and culture identifies FK1+VE-cadherin+ cells at a diverging point of endothelial and hemopoietic lineages" Development: vol. 125, pp. 1747-1757.
Soria, et al., (2000) "Insulin-Secreting Cells Derived From Embryonic Stem Cells Normalize Glycemia in Streptozotocin-Induced Diabetic Mice" Diabetes: vol. 49, pp. 1-6.
Li, et al., (1998) "Generationof purified neural precursors from embryonic stem cells by lineage selection" Current Biology vol. 8, pp. 971-974.
Braeckmans, et al., (2002) "Encoding Microcarriers: Present and Future Technologies" Nature Reviews in Drug Discovery: vol. 1, pp. 447-456.
Nicolaou et al., (1985) "Radiofrequency Encoded Combinatorial Chemistry" Angewandte Chemie (International ed. in English), vol. 34, pp. 2289-2291.

(Continued)

*Primary Examiner* — Vanessa L. Ford
*Assistant Examiner* — Lakia Tongue
(74) *Attorney, Agent, or Firm* — Steptoe & Johnson LLP

(57) ABSTRACT

A method for determining the effect of a plurality of culture conditions on a cell, comprising the steps of: a) providing a first set of groups of cell units each comprising one or more cells, and exposing said groups to desired culture conditions; (b) pooling two or more of said groups to form at least one second pool; (c) subdividing the second pool to create a further set of groups of cell units; (d) exposing said further groups to desired culture conditions; (e) optionally, repeating steps (b)-(d) iteratively as required; and (f) optionally assessing the effect on a given cell unit of the culture conditions to which it has been exposed.

12 Claims, 18 Drawing Sheets

OTHER PUBLICATIONS

Guiles, et al., (1998) "A Visual Tagging Process for Mix and Sort Combinatorial Chemistry" Angewandte Chemie (International ed. in English) vol. 37, pp. 926-928.

Xiao, et al., (1997) "Combinatorial Chemistry with Laser Optical Encoding" Angewandte Chemie (International ed. in English) vol. 36 pp. 780-782.

Geysen, et al., (1984) "Use of peptide synthesis to probe viral antigens for epitopes to a resolution of a singel amino acid" PNAS, vol. 81, pp. 3998-4002.

Fodor et al., (1991) "Light-Directed, Spatially Addressable Parallel Chemical Synthesis" Science, vol. 251, pp. 767-773.

Ziauddin et al., (2001) "Microarrays of cells expressing defined cDNAs" Nature, vol. 11 pp. 107-110.

Wu, et al., (2002) "Cell-biological applications fo transfected-cell microarrays" Trends in Cell Biology vol. 12, No. 10: pp. 485-488.

Wiles et al., (1999) "Embryonic Stem Cell Development in a Chemically Defined Medium" vol. 247 pp. 241-248.

Stem. Cells: Scientific Progress and Future Research Directions *The National Institute of Health* (2001).

Braeckmans, Kevin, et al., "Scanning the code encoded microcarrier beads signal the way to better combinatorial libraries and biological assays," *Modern Drug Discovery* (2003) pp. 28-32.

Johe, K. K., et al., "Single factors direct the differentiation of stem cells from the fetal and adult nervous system," *Genes Dev.* (1996) vol. 10 pp. 3129-3140.

Wagner, Joseph, et al., "Induction of a midbrian dopaminergic phenotype in *Nurr*1—overexpressing neural stem cells by type 1 astrocytes," *Nature Biotechnology* (1999) vol. 17 pp. 653-659.

Chen, L. R., et al., "Establishment of pluripotent cell lines from porcine preimplantation embryos," *Theriogenology* (1999) vol. 52 pp. 195-212 XP002961932.

Clark, J. M., et al., "Optimizing culture conditions for the production of animal cells in microcarrier culture," *Annals of the New York Academy of Science* (1981) vol. 369 pp. 33-46 XP002494705.

Visvikis, Athanase, et al., "Gamma Glutamyltransferase from human hepatoma cell lines: purification and cell culture of HEPG2 on microcarriers," *Clinical Chimica Acta* (1990) vol. 191 pp. 221-232. XP002494706.

Mannello, Ferdinando, et al., "Concise review: No breakthroughs for human mesenchymal and embryonic stem cell culture; conditioned medium, feeder layer, or feeder free; medium with fetal calf serum, human serum or enriched plasma, serum-free, serum replacement noncondition medium, or ad hoc formula? All that glitters is not gold!" *Stem Cell* (2007) vol. 25 pp. 1603-1609. XP002466979.

Okabe S. et al., Development of neuronal precursor cells and functional postmitotic neurons from embryonic stem cells in vitro, Mechanisms of Development, 1996, vol. 59, p. 89-102.

Wyzykowski JC et al., Mol. Cell. Bio., Sep. 2002, vol. 22, p6199-6208.

Bardouille C et al., Growth and differentiation of permanent and secondary mouse myogenic cell lines on microcarriers, Appl Microbiol. Biotechnol., 2001, vol. 55, p556-562.

Finkel et al. Anal. Chem. 2004 vol. 76, p352A-359A.

Kuchinke W. et al.: "Identification of mRNA's by Interferon-gamma in cultured rat astrocytes by PCR differential display" Neuroimmunomodulation, vol. 2, Jul. 1996, pp. 347-355 (D4).

Wong CKC et al., J Endocrin., Sep. 2002, vol. 173, p199-209.

\* cited by examiner

SEQUENCE LISTING

```
<160> NUMBER OF SEQ ID NOS: 48

<210> SEQ ID NO 1
<211> LENGTH: 67
<212> TYPE: DNA
<213> ORGANISM: Artificial sequence
<220> FEATURE:
<223> OTHER INFORMATION: Synthetic

<400> SEQUENCE: 1
tgcaggaatt cgcgctatgc taacgtgaag ccacgtcgcc gccgccgccg acccggccga      60
attcctg                                                              67

<210> SEQ ID NO 2
<211> LENGTH: 67
<212> TYPE: DNA
<213> ORGANISM: Artificial sequence
<220> FEATURE:
<223> OTHER INFORMATION: Synthetic

<400> SEQUENCE: 2
tgcaggaatt cgcgctatgc tgacgtgaag tcacgtcgcc accgccgccg acccggccga      60
attcctg                                                              67

<210> SEQ ID NO 3
<211> LENGTH: 67
<212> TYPE: DNA
<213> ORGANISM: Artificial sequence
<220> FEATURE:
<223> OTHER INFORMATION: Synthetic

<400> SEQUENCE: 3
tgcaggaatt cgcgctatgc tcacgtgaag acacgtcgcc tccgccgccg acccggccga      60
attcctg                                                              67

<210> SEQ ID NO 4
<211> LENGTH: 67
<212> TYPE: DNA
<213> ORGANISM: Artificial sequence
<220> FEATURE:
<223> OTHER INFORMATION: Synthetic

<400> SEQUENCE: 4
tgcaggaatt cgcgctatgc ttacgtgaag gcacgtcgcc cccgccgccg acccggccga      60
attcctg                                                              67
```

```
<210> SEQ ID NO 5
<211> LENGTH: 67
<212> TYPE: DNA
<213> ORGANISM: Artificial sequence
<220> FEATURE:
<223> OTHER INFORMATION: Synthetic

<400> SEQUENCE: 5
tgcaggaatt cgcgctatgc taacgtgaag acacgtcgcc agcgccgccg acccggccga    60
attcctg                                                              67

<210> SEQ ID NO 6
<211> LENGTH: 67
<212> TYPE: DNA
<213> ORGANISM: Artificial sequence
<220> FEATURE:
<223> OTHER INFORMATION: Synthetic

<400> SEQUENCE: 6
tgcaggaatt cgcgctatgc tagcgtgaag atacgtcgcc aacgccgccg acccggccga    60
attcctg                                                              67

<210> SEQ ID NO 7
<211> LENGTH: 67
<212> TYPE: DNA
<213> ORGANISM: Artificial sequence
<220> FEATURE:
<223> OTHER INFORMATION: Synthetic

<400> SEQUENCE: 7
tgcaggaatt cgcgctatgc taccgtgaag aaacgtcgcc atcgccgccg acccggccga    60
attcctg                                                              67

<210> SEQ ID NO 8
<211> LENGTH: 67
<212> TYPE: DNA
<213> ORGANISM: Artificial sequence
<220> FEATURE:
<223> OTHER INFORMATION: Synthetic

<400> SEQUENCE: 8
tgcaggaatt cgcgctatgc tatcgtgaag agacgtcgcc accgccgccg acccggccga    60
attcctg                                                              67

<210> SEQ ID NO 9
<211> LENGTH: 67
<212> TYPE: DNA
<213> ORGANISM: Artificial sequence
<220> FEATURE:
<223> OTHER INFORMATION: Synthetic

<400> SEQUENCE: 9
tgcaggaatt cgcgctatgc taaagtgaag acccgtcgcc acggccgccg acccggccga    60
attcctg                                                              67

<210> SEQ ID NO 10
<211> LENGTH: 67
<212> TYPE: DNA
<213> ORGANISM: Artificial sequence
<220> FEATURE:
<223> OTHER INFORMATION: Synthetic
```

-continued

```
<400> SEQUENCE: 10
tgcaggaatt cgcgctatgc taaggtgaag actcgtcgcc acagccgccg acccggccga    60
attcctg                                                              67

<210> SEQ ID NO 11
<211> LENGTH: 67
<212> TYPE: DNA
<213> ORGANISM: Artificial sequence
<220> FEATURE:
<223> OTHER INFORMATION: Synthetic

<400> SEQUENCE: 11
tgcaggaatt cgcgctatgc taacgtgaag acacgtcgcc actgccgccg acccggccga    60
attcctg                                                              67

<210> SEQ ID NO 12
<211> LENGTH: 67
<212> TYPE: DNA
<213> ORGANISM: Artificial sequence
<220> FEATURE:
<223> OTHER INFORMATION: Synthetic

<400> SEQUENCE: 12
tgcaggaatt cgcgctatgc taatgtgaag acgcgtcgcc accgccgccg acccggccga    60
attcctg                                                              67

<210> SEQ ID NO 13
<211> LENGTH: 67
<212> TYPE: DNA
<213> ORGANISM: Artificial sequence
<220> FEATURE:
<223> OTHER INFORMATION: Synthetic

<400> SEQUENCE: 13
tgcaggaatt cgcgctatgc taacatgaag acacgtcgcc accgccgccg acccggccga    60
attcctg                                                              67

<210> SEQ ID NO 14
<211> LENGTH: 67
<212> TYPE: DNA
<213> ORGANISM: Artificial sequence
<220> FEATURE:
<223> OTHER INFORMATION: Synthetic

<400> SEQUENCE: 14
tgcaggaatt cgcgctatgc taacgtgaag acatgtcgcc accaccgccg acccggccga    60
attcctg                                                              67

<210> SEQ ID NO 15
<211> LENGTH: 67
<212> TYPE: DNA
<213> ORGANISM: Artificial sequence
<220> FEATURE:
<223> OTHER INFORMATION: Synthetic

<400> SEQUENCE: 15
tgcaggaatt cgcgctatgc taacctgaag acaagtcgcc acctccgccg acccggccga    60
attcctg                                                              67
```

```
<210> SEQ ID NO 16
<211> LENGTH: 67
<212> TYPE: DNA
<213> ORGANISM: Artificial sequence
<220> FEATURE:
<223> OTHER INFORMATION: Synthetic

<400> SEQUENCE: 16
tgcaggaatt cgcgctatgc taacttgaag acaggtcgcc accccgccg acccggccga      60 attcctg                                                                67

<210> SEQ ID NO 17
<211> LENGTH: 67
<212> TYPE: DNA
<213> ORGANISM: Artificial sequence
<220> FEATURE:
<223> OTHER INFORMATION: Synthetic

<400> SEQUENCE: 17
tgcaggaatt cgcgctatgc taacgagaag acacctcgcc accggcgccg acccggccga      60
attcctg                                                                67

<210> SEQ ID NO 18
<211> LENGTH: 67
<212> TYPE: DNA
<213> ORGANISM: Artificial sequence
<220> FEATURE:
<223> OTHER INFORMATION: Synthetic

<400> SEQUENCE: 18
tgcaggaatt cgcgctatgc taacgggaag acacttcgcc accgacgccg acccggccga      60
attcctg                                                                67

<210> SEQ ID NO 19
<211> LENGTH: 67
<212> TYPE: DNA
<213> ORGANISM: Artificial sequence
<220> FEATURE:
<223> OTHER INFORMATION: Synthetic

<400> SEQUENCE: 19
tgcaggaatt cgcgctatgc taacgcgaag acacatcgcc accgtcgccg acccggccga      60
attcctg                                                                67

<210> SEQ ID NO 20
<211> LENGTH: 67
<212> TYPE: DNA
<213> ORGANISM: Artificial sequence
<220> FEATURE:
<223> OTHER INFORMATION: Synthetic

<400> SEQUENCE: 20
tgcaggaatt cgcgctatgc taacgtgaag acacgtcgcc accgccgccg acccggccga      60
attcctg                                                                67

<210> SEQ ID NO 21
<211> LENGTH: 67
<212> TYPE: DNA
<213> ORGANISM: Artificial sequence
<220> FEATURE:
<223> OTHER INFORMATION: Synthetic
```

-continued

```
<400> SEQUENCE: 21
tgcaggaatt cgcgctatgc taacgtaaag acacgccgcc accgcggccg acccggccga      60
attcctg                                                                67

<210> SEQ ID NO 22
<211> LENGTH: 67
<212> TYPE: DNA
<213> ORGANISM: Artificial sequence
<220> FEATURE:
<223> OTHER INFORMATION: Synthetic

<400> SEQUENCE: 22
tgcaggaatt cgcgctatgc taacgtgaag acacgtcgcc accgcagccg acccggccga      60
attcctg                                                                67

<210> SEQ ID NO 23
<211> LENGTH: 67
<212> TYPE: DNA
<213> ORGANISM: Artificial sequence
<220> FEATURE:
<223> OTHER INFORMATION: Synthetic

<400> SEQUENCE: 23
tgcaggaatt cgcgctatgc taacgtcaag acacgacgcc accgctgccg acccggccga      60
attcctg                                                                67

<210> SEQ ID NO 24
<211> LENGTH: 67
<212> TYPE: DNA
<213> ORGANISM: Artificial sequence
<220> FEATURE:
<223> OTHER INFORMATION: Synthetic

<400> SEQUENCE: 24
tgcaggaatt cgcgctatgc taacgttaag acacggcgcc accgccgccg acccggccga      60
attcctg                                                                67

<210> SEQ ID NO 25
<211> LENGTH: 20
<212> TYPE: DNA
<213> ORGANISM: Artificial sequence
<220> FEATURE:
<223> OTHER INFORMATION: Synthetic, PCR primer

<400> SEQUENCE: 25
tgcaggaatt cgcgctatgc                                                  20

<210> SEQ ID NO 26
<211> LENGTH: 20
<212> TYPE: DNA
<213> ORGANISM: Artificial sequence
<220> FEATURE:
<223> OTHER INFORMATION: Synthetic, PCR primer

<400> SEQUENCE: 26
caggaattcg gccgggtcgg                                                  20

<210> SEQ ID NO 27
<211> LENGTH: 25
<212> TYPE: DNA
<213> ORGANISM: Artificial sequence
<220> FEATURE:
<223> OTHER INFORMATION: Synthetic, PCR primer
```

```
<400> SEQUENCE: 27
ccatgaccta tactcaggct tcagg                                          25

<210> SEQ ID NO 28
<211> LENGTH: 26
<212> TYPE: DNA
<213> ORGANISM: Artificial sequence
<220> FEATURE:
<223> OTHER INFORMATION: Synthetic, PCR primer

<400> SEQUENCE: 28
gaagctccat atccctgggt ggaaag                                         26

<210> SEQ ID NO 29
<211> LENGTH: 23
<212> TYPE: DNA
<213> ORGANISM: Artificial sequence
<220> FEATURE:
<223> OTHER INFORMATION: Synthetic, PCR primer

<400> SEQUENCE: 29
ccaaagtggt ggacaagatt gcc                                            23

<210> SEQ ID NO 30
<211> LENGTH: 24
<212> TYPE: DNA
<213> ORGANISM: Artificial sequence
<220> FEATURE:
<223> OTHER INFORMATION: Synthetic, PCR primer

<400> SEQUENCE: 30
gggataggaa ggacgctcaa agac                                           24

<210> SEQ ID NO 31
<211> LENGTH: 24
<212> TYPE: DNA
<213> ORGANISM: Artificial sequence
<220> FEATURE:
<223> OTHER INFORMATION: Synthetic, PCR primer

<400> SEQUENCE: 31
cagatgtagt ccgccaaagg atag                                           24

<210> SEQ ID NO 32
<211> LENGTH: 26
<212> TYPE: DNA
<213> ORGANISM: Artificial sequence
<220> FEATURE:
<223> OTHER INFORMATION: Synthetic, PCR primer

<400> SEQUENCE: 32
atgccactga tggagtatga ggagcc                                         26

<210> SEQ ID NO 33
<211> LENGTH: 24
<212> TYPE: DNA
<213> ORGANISM: Artificial sequence
<220> FEATURE:
<223> OTHER INFORMATION: Synthetic, PCR primer

<400> SEQUENCE: 33
tcaagactga ctcacagcaa cccc                                           24
```

```
<210> SEQ ID NO 34
<211> LENGTH: 24
<212> TYPE: DNA
<213> ORGANISM: Artificial sequence
<220> FEATURE:
<223> OTHER INFORMATION: Synthetic, PCR primer

<400> SEQUENCE: 34
ctttgtcctg aaccgtggtg gtag                                          24

<210> SEQ ID NO 35
<211> LENGTH: 20
<212> TYPE: DNA
<213> ORGANISM: Artificial sequence
<220> FEATURE:
<223> OTHER INFORMATION: Synthetic, PCR primer

<400> SEQUENCE: 35
acctgttgac ggattccaag                                               20

<210> SEQ ID NO 36
<211> LENGTH: 20
<212> TYPE: DNA
<213> ORGANISM: Artificial sequence
<220> FEATURE:
<223> OTHER INFORMATION: Synthetic, PCR primer

<400> SEQUENCE: 36
tcatgaggaa gcgtaggtcc                                               20

<210> SEQ ID NO 37
<211> LENGTH: 23
<212> TYPE: DNA
<213> ORGANISM: Artificial sequence
<220> FEATURE:
<223> OTHER INFORMATION: Synthetic, PCR primer

<400> SEQUENCE: 37
tgaagagagc ggagaaggag atc                                           23

<210> SEQ ID NO 38
<211> LENGTH: 24
<212> TYPE: DNA
<213> ORGANISM: Artificial sequence
<220> FEATURE:
<223> OTHER INFORMATION: Synthetic, PCR primer

<400> SEQUENCE: 38
tctggagtta agaaatcgga gctg                                          24

<210> SEQ ID NO 39
<211> LENGTH: 20
<212> TYPE: DNA
<213> ORGANISM: Artificial sequence
<220> FEATURE:
<223> OTHER INFORMATION: Synthetic, PCR primer

<400> SEQUENCE: 39
ggagtgtcgc ttagaggtgc                                               20

<210> SEQ ID NO 40
<211> LENGTH: 20
<212> TYPE: DNA
<213> ORGANISM: Artificial sequence
<220> FEATURE:
<223> OTHER INFORMATION: Synthetic, PCR primer
```

```
<400> SEQUENCE: 40
tccagaaagc caagagaagc                                           20

<210> SEQ ID NO 41
<211> LENGTH: 19
<212> TYPE: DNA
<213> ORGANISM: Artificial sequence
<220> FEATURE:
<223> OTHER INFORMATION: Synthetic, PCR primer

<400> SEQUENCE: 41
ggacaaggga aatgagagg                                            19

<210> SEQ ID NO 42
<211> LENGTH: 21
<212> TYPE: DNA
<213> ORGANISM: Artificial sequence
<220> FEATURE:
<223> OTHER INFORMATION: Synthetic, PCR primer

<400> SEQUENCE: 42
ataacacctc actccactac c                                         21

<210> SEQ ID NO 43
<211> LENGTH: 19
<212> TYPE: DNA
<213> ORGANISM: Artificial sequence
<220> FEATURE:
<223> OTHER INFORMATION: Synthetic, PCR primer

<400> SEQUENCE: 43
agtcagagca agtgaatgg                                            19

<210> SEQ ID NO 44
<211> LENGTH: 20
<212> TYPE: DNA
<213> ORGANISM: Artificial sequence
<220> FEATURE:
<223> OTHER INFORMATION: Synthetic, PCR primer

<400> SEQUENCE: 44
agaaacaaga tctcagcagg                                           20

<210> SEQ ID NO 45
<211> LENGTH: 24
<212> TYPE: DNA
<213> ORGANISM: Artificial sequence
<220> FEATURE:
<223> OTHER INFORMATION: Synthetic, PCR primer

<400> SEQUENCE: 45
cgcgttctct ttggaaaggt gttc                                      24

<210> SEQ ID NO 46
<211> LENGTH: 20
<212> TYPE: DNA
<213> ORGANISM: Artificial sequence
<220> FEATURE:
<223> OTHER INFORMATION: Synthetic, PCR primer

<400> SEQUENCE: 46
ctcgaaccac atccttctct                                           20
```

```
<210> SEQ ID NO 47
<211> LENGTH: 20
<212> TYPE: DNA
<213> ORGANISM: Artificial sequence
<220> FEATURE:
<223> OTHER INFORMATION: Synthetic, PCR primer

<400> SEQUENCE: 47
accacagtcc atgccatcac                                               20

<210> SEQ ID NO 48
<211> LENGTH: 20
<212> TYPE: DNA
<213> ORGANISM: Artificial sequence
<220> FEATURE:
<223> OTHER INFORMATION: Synthetic, PCR primer

<400> SEQUENCE: 48
tccaccaccc tgttgctgta                                               20
```

CELL CULTURE

FIELD OF THE INVENTION

The invention relates to cell culture, and in particular to the culture of primary cells, cell lines, pluripotent cells, totipotent cells and stem cells and the regulation of their various cellular processes through modulation of cell culture conditions. The invention relates to the use of multiple culture steps under a plurality of conditions to modulate cellular pathways and provides methods for determining the effect of diverse multiple culture step regimes on cellular processes such as growth, differentiation and metabolic activity.

BACKGROUND TO THE INVENTION

Over recent years cell culture has become a core technology in the life sciences. Cell culture is described in 'Basic Cell Culture' Oxford University Press (2002) Ed. J. M. Davis; and 'Animal Cell Culture' Oxford University Press (2000) Ed. John R. W. Masters; both of which are incorporated herein in their entirety by reference. Cell culture provides the basis for studying cellular processes such as the viability, phenotype, genotype, proliferation and differentiation of cells, and the formation of biological molecules, intermediates and products. It has also provided the means to study the regulation of these processes, from the genetic level—whether in isolation or in whole transgenic animals—down to the level of individual protein molecules. Notwithstanding its enormous contribution to the current state of biology, in many respects cell culture remains a developing discipline, albeit an unusually exciting science ultimately offering the possibility of genetic therapy and tissue engineering.

An important goal of cell culture is to be able to grow a wide variety of cells in vitro. The list of different cell types that can be grown in culture is extensive (see American Type Culture collection, European Collection of Cell Cultures, Deutsche Sammlung von Mikroorganismen and Zellkulturen GmbH,), includes representatives of most cell types, and is continually increasing as more and more culture conditions are discovered. Despite the steady progress in the field, the method of determining suitable culture conditions for new cell types remains totally empirical: growth conditions are almost always discovered by trial and error. The choice of starting point will often be based on what was previously used by others for similar cells, or even what is currently being used in the laboratory for different cells. Many times these will simply be completely inadequate, and a process of trial and error must begin anew. Even when new culture conditions are successful, it is worthwhile remembering that adaptations of previous protocols will have introduced a historical bias to the experiment. For instance, much of the early tissue culture experiments made extensive use of fibroblasts, and to this date most standard cell culture conditions favour growth of cells derived from the mesoderm (fibroblasts, endothelium, myoblasts). The development of selective growth media for epithelial and other cell types based on these conditions was a challenge. For some of these cell types it is now known that serum—a normal component of many culture media for mesodermal cells—actually inhibits growth. One aspect of the invention described herein is a method for developing suitable culture conditions which allow for the viability, proliferation or growth, and retention of the phenotype of particular cell types.

Apart from conditions that favour cell proliferation, a particularly important step in modern tissue culture is to be able to control or direct the differentiation of cells towards a particular phenotype. As propagation of cell lines requires that the cell number increases, the vast majority of culture conditions have been developed to favour maximal cell proliferation. It is not surprising that these conditions are not conducive to cell differentiation, where cell growth is often limited or even abolished. The conditions which favour cell proliferation are generally low cell density, low $Ca^{2+}$ concentration, and the presence of growth factors such as epidermal growth factor (EGF), fibroblast growth factor (FGF) and platelet-derived growth factor (PDGF). On the other hand, cytostasis and differentiation are promoted in conditions of high cell density, high $Ca^{2+}$ concentration and the presence of differentiation Inducers such as hormones (e.g. hydrocortisone), paracrine factors (e.g. IL-6, KGF, NGF), retinoids and even planar polar compounds such as dimethylsulphoxide (DMSO). Hence different conditions may be required for propagation and for differentiation of a particular cell line, and of course these respective conditions may differ between cells of different lineages. A second aspect of the invention described herein is a method for discovering suitable culture conditions which allow for the selective differentiation of cells.

Some common problems which are still encountered in cell culture are the limited lifespan of primary cell lines, the change of characteristics of cell lines with passage, and their transformation accompanied by loss of interesting cellular characteristics. These effects severely limit the utility of cultured cells for use in experiments or assays, for instance cell-based assays described below. Primary cells, i.e. cells freshly isolated from tissues, offer by far the most accurate cell culture models, as they behave in a way that broadly resembles their tissue of origin. Remarkably, a reliable method of culturing primary cells has still not been developed and consequently these cells exhibit a limited lifespan in vitro. This presents a serious technical limitation, for instance when attempting to amplify the primary culture, or when attempting to perform a longer-term experiment. A further problem associated with the use of primary cultures is that since they require constant fresh isolation, it can be hard to source primary material, particularly from humans and it is also difficult to obtain lines that behave consistently. A third aspect of the invention is therefore a method of culturing primary cells to obtain viable cultures with a prolonged lifespan.

If primary cultures are maintained in vitro for an extended period, they normally undergo a crisis in which the majority of cells perish, however the surviving cells are longer lived and can be cultured indefinitely. Most of these continuous cell lines are almost invariably poor representations of the cell as it is found in intact animal tissues. One reason for this lies in the fact that the process that allows the cells to become immortal also has an impact on the characteristics of the cell. For example, most established cell cultures have stopped expressing tissue-specific genes and instead only express housekeeping genes required for continuous growth in cell culture—as a result most such cell lines are more like each other than like the tissue from which they were originally sourced. For instance, most liver cell lines have stopped expressing the drug-metabolizing enzymes that would normally make them interesting tools for testing drug toxicity. A further aspect of the invention described herein is a method of culturing cells so that they provide more accurate models of tissues. This in turn would improve the reliability and predictive power of cell-based experiments and assays.

There is a need in the art for improved techniques for culturing cells, and methods for discovering and implementing such techniques for regulation of cellular processes such as growth, differentiation, metabolic activity, and phenotypic expression.

SUMMARY OF THE INVENTION

The present invention provides novel cell culture techniques which are based on the perception that cell culture is better approached as a dynamic process involving serial culture steps performed in a defined sequence to achieve a desired effect. The invention recognises that sequential exposure to selected agents may be exploited to modulate cellular processes and thus achieve a level of control over these which was not previously attainable by conventional techniques.

The invention addresses the problem that cell culture techniques involving a plurality of steps and agents are in practice difficult if not impossible to determine by conventional experimentation, which in the prior art has involved trial and error. Owing to the cumbersome nature of conventional cell culture, empirical determination of tissue culture conditions in complex, multi-stage procedures is not feasible in practice as it involves massive work loads.

In a first aspect, the invention provides a method for determining the effect of a plurality of culture conditions on a cell, comprising the steps of:
 (a) providing a first set of groups of cell units each comprising one or more cells, and exposing said groups to desired culture conditions;
 (b) subdividing one or more of said groups to create a further set of groups of cell units;
 (c) exposing said further groups to further desired culture conditions;
 (d) optionally, repeating steps (b)-(c) iteratively as required; and
 (e) assessing the effect on a given cell unit of the culture conditions to which it has been exposed.

Advantageously, the groups of cells according to the invention are pools and subsequently split. Thus, in a preferred embodiment, the invention provides a method for determining the effect of a plurality of culture conditions on a cell, comprising the steps of:
 (a) providing a first set of groups of cell units each comprising one or more cells, and exposing said groups to desired culture conditions;
 (b) pooling two or more of said groups to form at least one pool;
 (c) subdividing the pool to create a further set of groups of cell units;
 (d) exposing said further groups to desired culture conditions;
 (e) optionally, repeating steps (b)-(d) iteratively as required; and
 (f) assessing the effect on a given cell unit of the culture conditions to which it has been exposed.

The invention addresses all cellular processes including the phenotype, genotype, molecule production, viability, and the proliferation and differentiation of cells. Preferably, the invention is used to identify conditions which result in cellular differentiation. For example cells may be induced to differentiate along a desired developmental pathway, by subjecting the cells to appropriate culture conditions. The timing of the changing of culture conditions is also exploited to better define the developmental programme of the cells.

Culture conditions include growth media, chemical, molecular, and macromolecular agents present in growth media, temperature regimes, substrates, atmospheric conditions, physical cell handling and the like.

The above method of the invention, known as combinatorial cell culture, or split-pool culturing, allows cells to be subjected to a series of culture conditions, and exposed to a series of agents in culture media, in a systematic and highly productive manner.

Although repetitive cycles of splitting and pooling may be used highly efficiently, in a similar manner to combinatorial chemistry protocols, given the necessary processing power protocols involving at least two sequential splitting steps (without re-pooling) may be used. The disadvantage of such protocols is that they can quickly generate a very large number of separate samples, which have been handled differently. The advantage, however, is that each sample does not require laborious deconvolution, since the cell units therein have only been exposed to one set of conditions. Accordingly, given suitable sample handling facilities, a splitting approach can yield rapid results.

The invention employs cell units. Such units may be single cells, but are advantageously colonies of two or more cells, which are arranged in such a form that they are resistant to disruption even during split pool culturing procedures. For instance, the cells may be cultured on a solid substrate, such as beads, as described in more detail below.

Advantageously, the cell units are labelled. Labelling allows the following of the culture conditions to which the cells have been exposed, or the following of cell units as they are exposed to different culture conditions; thus, any given cell unit can have its label read in order to determine how it has been derived from the starter cell pool or culture. Labels may take any of a variety of molecular or physical forms, including nucleic acid labels, radiofrequency encoded tags, fluorescent or optical tags, and spatial encoding of cell units on a surface or matrix.

The method of the invention allows thousands or millions of cell culture conditions and reagents to be tested, in a multiplexed high-throughput assay, to determine the conditions necessary to achieve the desired result with respect to any cellular process.

Therefore, the invention provides a method for exposing a cell to a variety of cell culture conditions, comprising the steps of:
 (a) providing a first set of groups of cell units each comprising one or more cells, and exposing said groups to desired culture conditions;
 (b) subdividing one or more of said groups to create a further set of groups of cell units;
 (c) exposing said further groups to further desired culture conditions; and
 (d) optionally, repeating steps (b)-(c) iteratively as required.

In a preferred embodiment, as referred to above, a pooling procedure is employed. In such an embodiment, the invention provides a method for determining the effect of a plurality of culture conditions on a cell, comprising the steps of:
 a) providing a first set of groups of cell units each comprising one or more cells, and exposing said groups to desired culture conditions;
 (b) pooling two or more of said groups to form at least one second pool;
 (c) subdividing the second pool to create a further set of groups of cell units;
 (d) exposing said further groups to desired culture conditions;
 (e) optionally, repeating steps (b)-(d) iteratively as required; and
 (f) assessing the effect on a given cell unit of the culture conditions to which it has been exposed.

In a further aspect, the invention provides a method for identifying a gene which influences a cellular process, comprising the steps of:
  a) determining the effect of one or more culture conditions on a cell unit, in accordance with the foregoing aspect of the invention;
  b) analysing gene expression in said cell units when exposed to said culture conditions; and
  c) identifying genes which are differentially expressed under desired culture conditions.

Advantageously, the culture conditions used cause a change in the cellular process; these culture conditions are selected for the production of cells in which gene expression is analysed. Gene expression may conveniently be analysed using any comparative expression monitoring technology including PCR-based techniques, Serial Analysis of Gene Expression (SAGE), or array technology such as is widely available from suppliers such as Affymetrix.

In another aspect, the invention provides a method for producing a nucleic acid which encodes a gene product which influences a cellular process, comprising identifying a gene as above, and producing at least the coding region of said gene by nucleic acid synthesis or biological replication.

In a further aspect, there is provided a method for inducing a cellular process in a cell, comprising the steps of:
  a) identifying one or more genes which are differentially expressed in association with a cellular process in accordance with the invention; and
  b) modulating the expression of said one or more genes in the cell.

The expression of the genes in the cell can be modulated by, for example, transfecting or otherwise transferring the gene into the cell such that it is overexpressed in a transient or permanent manner. Alternatively, the expression of the endogenous gene may be altered, such as by targeted enhancer insertion or the administration of exogenous agents which cause an increase (e.g. gratuitous inducers) or decrease (e.g. antisense, RNAi, transcription factors) in the expression of the gene. Moreover, the product of the gene may itself be administered to or introduced into the cell to achieve an increase in its activity. Furthermore, agents which increase or decrease the activity of the gene product (e.g. competitive and non-competitive Inhibitors, drugs, pharmaceuticals) can be administered to the cell.

In a still further aspect, the invention provides a method for identifying the state of a cellular process in a cell, comprising the steps of:
  a) identifying one or more genes which are differentially expressed in association with a cellular process as set forth above; and
  b) detecting the modulation of expression of said one or more genes in a cell, thereby determining the state of the cellular process in said cell.

Advantageously, the genes employed in this analysis encode cellular markers, which may be detected for instance by immunoassay. Alternatively, the gene products may be enzymes that can be assayed for activity with fluorometric, colourometric, radiometric, or other methodologies.

The invention further provides a method for regulating a cellular process, comprising the steps of:
  a) determining the effect of one or more culture conditions on a cell unit, in accordance with the foregoing aspect of the invention;
  b) exposing a cell to culture conditions which effect a change in the cellular process; and
  c) isolating the desired cell.

Accordingly the invention provides for a method for producing a differentiated cell from a bipotent, pluripotent or totipotent progenitor, in accordance with the foregoing aspect of the invention. Differentiated cells, particularly partly differentiated, pluripotent cells, or developmentally committed but undifferentiated progenitor cells are useful in drug discovery, cellular therapies and other procedures in which cells of a defined lineage are required.

There is also provided a method for identifying an agent which is capable of inducing a cellular process, comprising the steps of:
  a) determining the effect of one or more agents on a cell unit, in accordance with the foregoing aspect of the invention; and
  b) identifying those agent(s) which induce the desired cellular process in the cell units.

Agents identified in accordance with the invention may be synthesised by conventional chemical, biochemical or other techniques, and used in methods for regulating particular cellular processes in cells for example as described herein.

The invention moreover broadly provides methods of culturing cells adherent to solid carriers such as microcarriers or beads. Such carriers can be composed of macromolecules such as cellulose, dextran, agarose, or acrylamide, or inorganic materials such as glass. The surfaces of the carriers may be further modified by physical or chemical treatments, such as adsorption or covalent cross-linking of molecular entities with a desired charge or other desired characteristic. Alternatively, the carrier may consist of a cell or cells encapsulated within a matrix that allows perfusion of sub-cellular sized material. Microcarrier culture has significant advantages, including the scale-up of cultures, and also allows cell units to be conveniently exposed to selected culture conditions as required in order to cause the desired cellular process. In the broadest embodiment, therefore, the invention provides a method for culturing cells in vitro, comprising growing said cells adhered to a microcarrier or bead.

Advantageously, the cells are subjected to at least one change of culture conditions. Preferably, they are subjected to 2, 3, 4, 5, 6, 7, 8, 9, or 10 or more different culture conditions. Preferably, said change of culture conditions comprises a change of medium.

The invention moreover provides methods for culturing cells in which pools of cells are created and subdivided as described for the preceding embodiments of the invention. Thus, in one aspect, there is provided a method for culturing cells in vitro, comprising the steps of
  a) combining one or more cultures of cells grown under different conditions; and
  b) culturing the cells under common conditions.

In further embodiment, there is provided a method for culturing cells in vitro, comprising the steps of:
  a) incubating a cell culture; and
  b) splitting said culture into two or more groups of cells, and culturing said group of cells under two or more different sets of culture conditions.

Preferably, the cells are exposed to 3, 4, 5, 6, 7, 8, 9, 10 or more different culture conditions. The culture conditions used advantageously comprise a change of medium. The invention moreover broadly provides methods of culturing stem cells, and differentiated cells derived from stem cells in vitro, adherent to microcarriers, such as beads. Microcarrier culture has significant advantages, including the scale-up of cultures, and also allows units of stem cells to be exposed to selected culture conditions as required in order to obtain the desired growth and/or differentiation conditions. In one embodiment, therefore, the invention provides a method for culturing stem cells and differentiated cells derived from stem cells in vitro, comprising growing said cells adhered to a microcarrier or bead.

Advantageously, the culture is subjected to at least one change of culture conditions. Preferably, they are subjected to 2, 3, 4, 5, 6, 7, 8, 9, or 10 or more different culture conditions. Preferably, said change of culture conditions comprises a change of medium.

The invention moreover provides methods for culturing stem cells in which pools of stem cells are created and subdivided as described for the preceding embodiments of the invention. Thus, in one aspect, there is provided a method for culturing stem cells and differentiated cells derived from stem cells in vitro, comprising the steps of:

a) combining one or more cultures of cells grown under different conditions; and
b) culturing the cells under common conditions.

In further embodiment, there is provided a method for culturing stem cells and differentiated cells derived from stem cells in vitro, comprising the steps of:

a) incubating a stem cell culture; and
b) splitting said culture into two or more groups of stem cells, and culturing said group of stem cells under two or more different sets of culture conditions.

Preferably, the cells are exposed to 3, 4, 5, 6, 7, 8, 9, 10 or more different culture conditions. The culture conditions used advantageously comprise a change of medium.

Advantageously, cells or stem cells are cultured in cell units, each cell unit comprising one or more such cells. For example, the cell units can be single cells.

However, each cell unit can comprise one or more cells or stem cells adherent to or bounded by a solid substrate, such as a microcarrier or bead. Further solid substrates include a well or medium-permeable barrier.

Methods for culturing cells or stem cells according to the invention may be scaled up in suitable bioreactors. For example, the method of the invention may be practised using more than 50 g dry weight of microcarrier.

Panel I shows a composite image obtained by fluorescence microscopy showing differentiated embryonic stem cells growing on a non porous microcarrier (CYTODEX 3, Amersham Biosciences). The cells express a Tau-GFP and are immunochemically stained red with a fluorescent antibody raised against the neuron-specific protein beta-tubulin III. Yellow colouration indicates coincident red and green staining.

Figure 9:
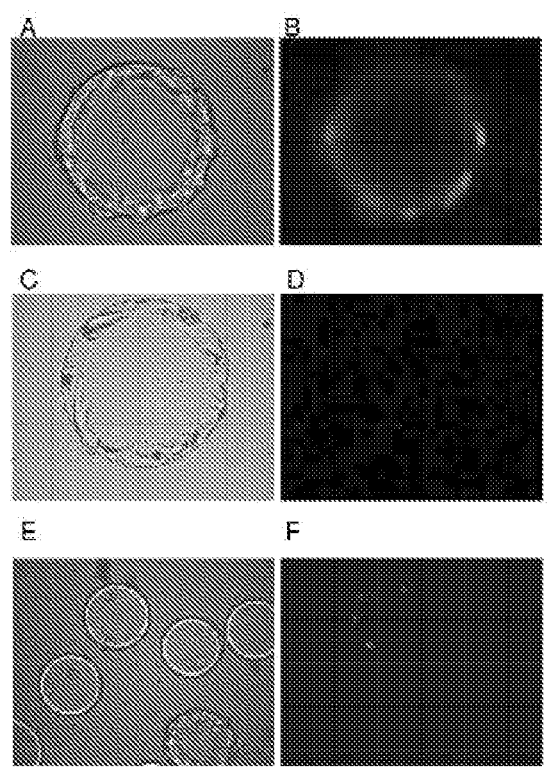

FIG. 9 shows phase (Panels A, C, E) and fluorescent (Panels B, D, F) microphotographs of cell units comprising HepG2 cells attached to non-porous microcarriers (CYTODEX 3, Amersham Biosciences). Panels A/B: positive control cell unit showing conversion of ethoxyresorufin to a red fluorescent product; Panels C/D: negative control cell unit cultured in the same manner but to which no ethoxyresorufin was added; Panels E/F: cell units following a split pool experiment, showing that some cell units treated with the P450 inducer beta-naphthoflavone have high levels of P450 and are capable of rapidly converting ethoxyresorufin to fluorescent product (Panel F) while other cell units subjected to split-pool culture have are populated by a large number of cells that do not express high levels of P450 (eg. Cell unit evident at bottom right of Panel E.

Figure 10:
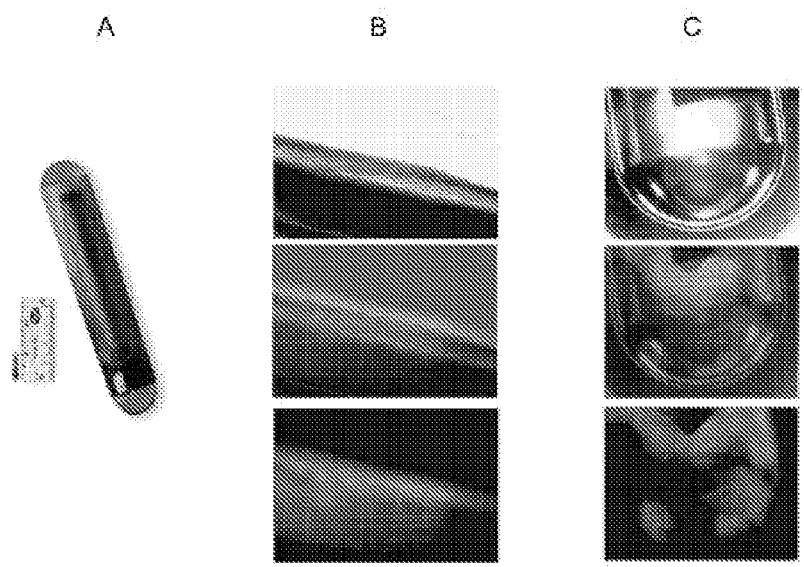

FIG. 10 shows labelling of cell units using RFID. Panel A: glass encapsulated radiofrequency transponder ID100-A (Trovan); Panel B: mouse embryonic stem cells expressing a Tau-GFP fusion protein growing on the straight edge of a glass encapsulated radiofrequency transponder (light microscopy, top; fluorescence microscopy, bottom; merged image, centre); (C) shows embryonic stem cells expressing GFP growing on the rounded end of a glass encapsulated radiofrequency transponder (light microscopy, top; fluorescence microscopy, bottom; merged image, centre).

Figure 11:
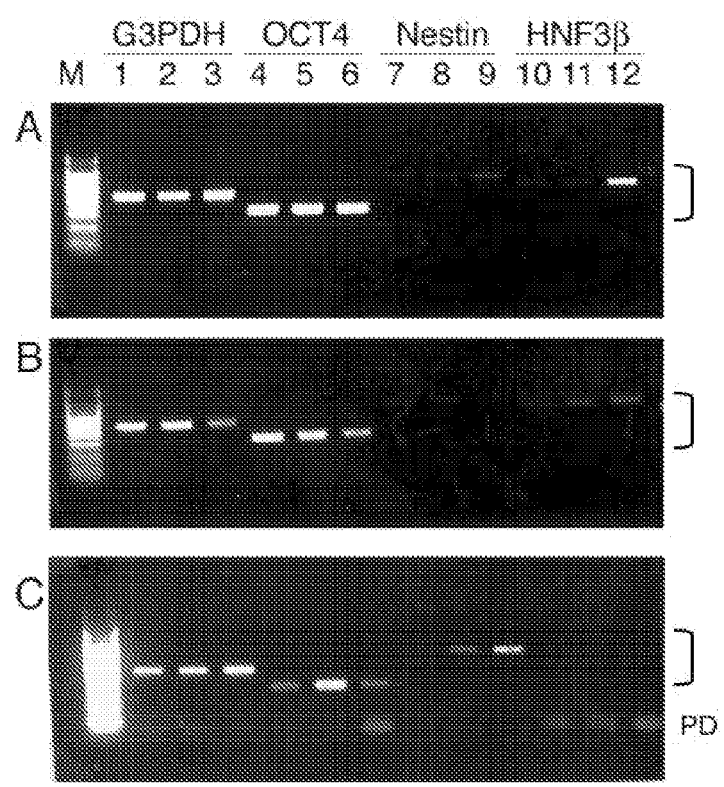

FIG. 11 illustrates differential gene expression following split-pool culture of mouse ES cells. ES cells were grown on CYTOPORE 2 microcarriers in ES medium (A), CDM (B), or DMEM (C) with no additions (lanes 1, 4, 7, 10), or with 1 µM LiCl (2, 5, 8, 11), or 1 µM Retinoic Acid (3, 6, 9, 12). cDNA was prepared from the cells and equivalent amounts were subjected to PCR with oligonucleotide primers for the control gene glyceraldehyde 3 phosphate dehydrogenase (G3PDH), and markers of undifferentiated ES cells (Oct4), neuronal precursors (Nestin), and endodermal cells (HNF3β). The photographs are of ethidium bromide-stained agarose gels of the PCR products, which are indicated by open brackets. 'PD' indicates primer-dimer products.

Figure 12:
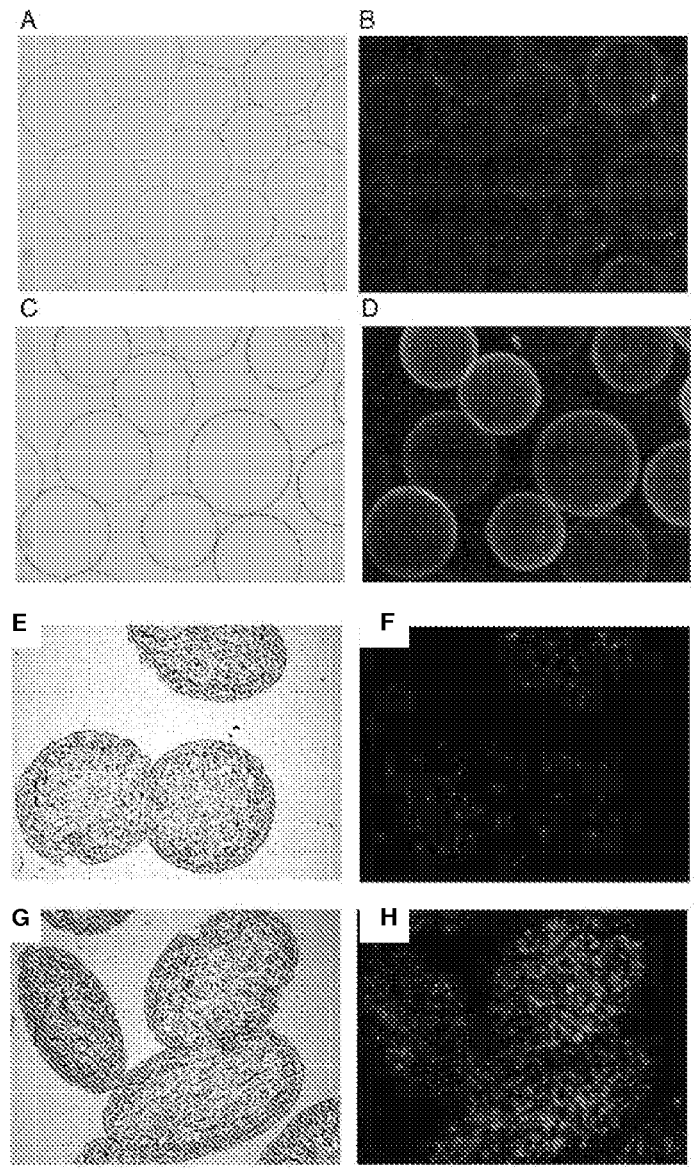

FIG. 12 shows labeling of microcarriers. Panels A-D: CYTODEX 3 microcarriers incubated without (A, B) or with (C, D) a biotinylated anti-collagen antibody, stained with streptavidin-FITC and viewed under phase (A, C) and fluorescence (B, D) microscopy. Panels E-H: CULTISPHER G microcarriers without (E, F) or with (G, H) cross linked biotin moieties, stained with streptavidin-coated 1 µm diameter red fluorescent beads and viewed under phase (E, G) and fluorescence (F, H) microscopy.

Figure 13:
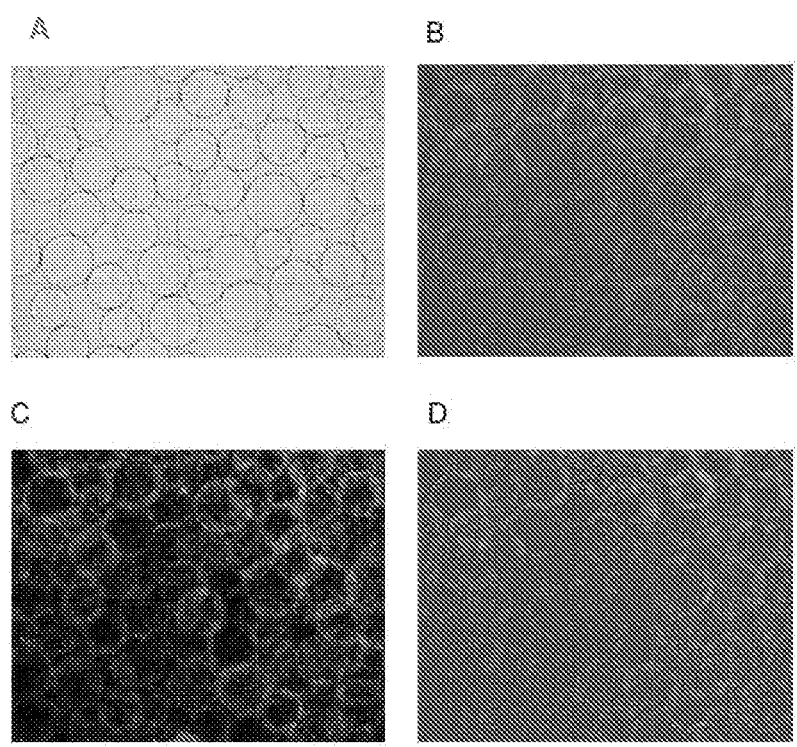

FIG. 13 shows labelling of two populations of microcarriers with two different fluorescent labels. CYTODEX 3 microcarriers were incubated separately with red or green streptavidin latex beads, then mixed in a 1:1 ratio. They were viewed using phase microscopy (A) and with filters to detect green (C) or red (D) fluorescence. B is a merged photograph of C+D. Both labels are readily detected, and no significant transfer of labels was detected.

Figure 14:
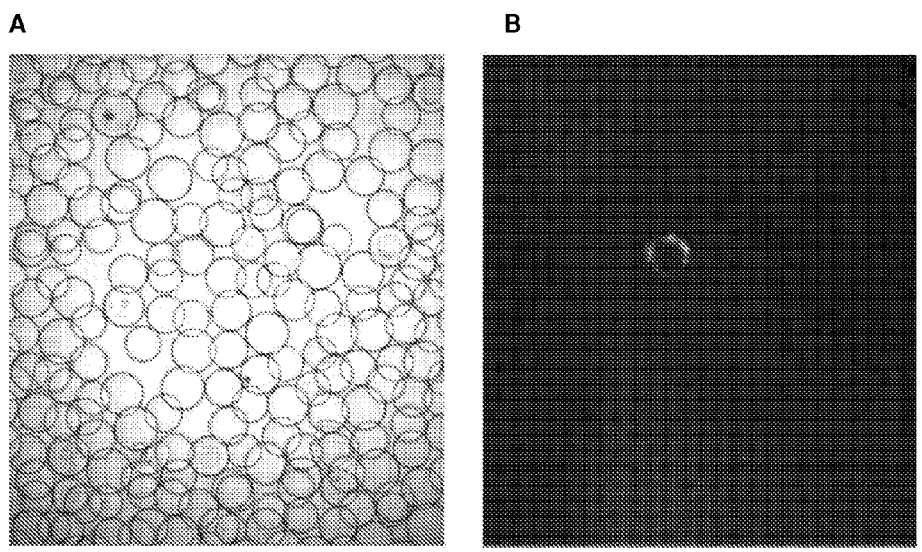

FIG. 14 illustrates the double-labelling of microcarriers with two different fluorescent labels. CYTODEX 3 microcarriers were incubated with a 1:1 mixture of red and green streptavidin latex beads. They were viewed under phase microscopy (A) and with filters to detect green (C) or red (D) fluorescence. B is a merged photograph of C+D. Each microcarrier is doubly labeled.

Figure 15:
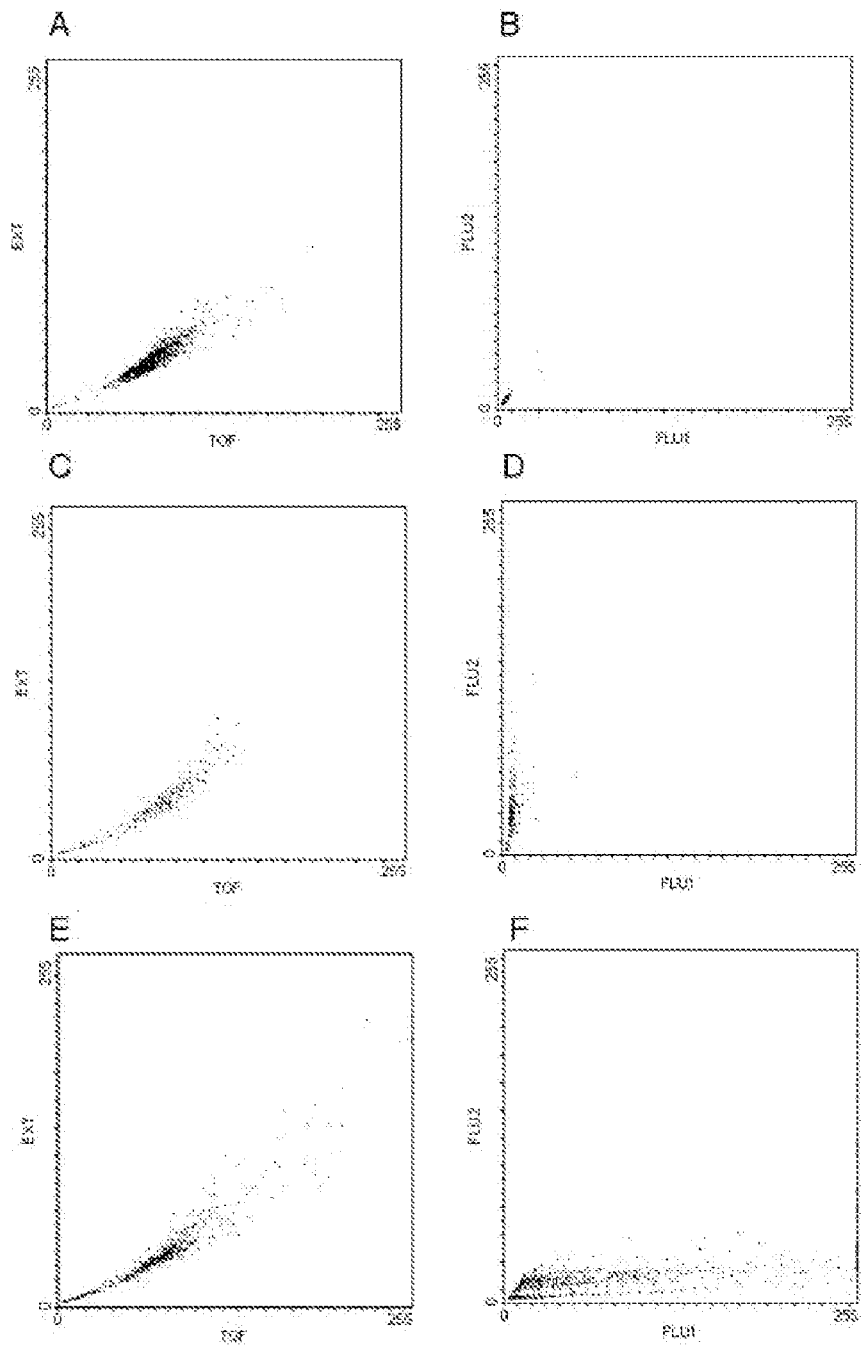

FIG. 15 shows detection of a cell unit exhibiting a cellular process using phase (Panel A) or fluorescence (Panel B) microscopy. Cell units expressing a Tau-GFP fusion protein can be readily discriminated from the background using fluorescence microscopy (B) and can be manually isolated from the mixture.

Figure 16:
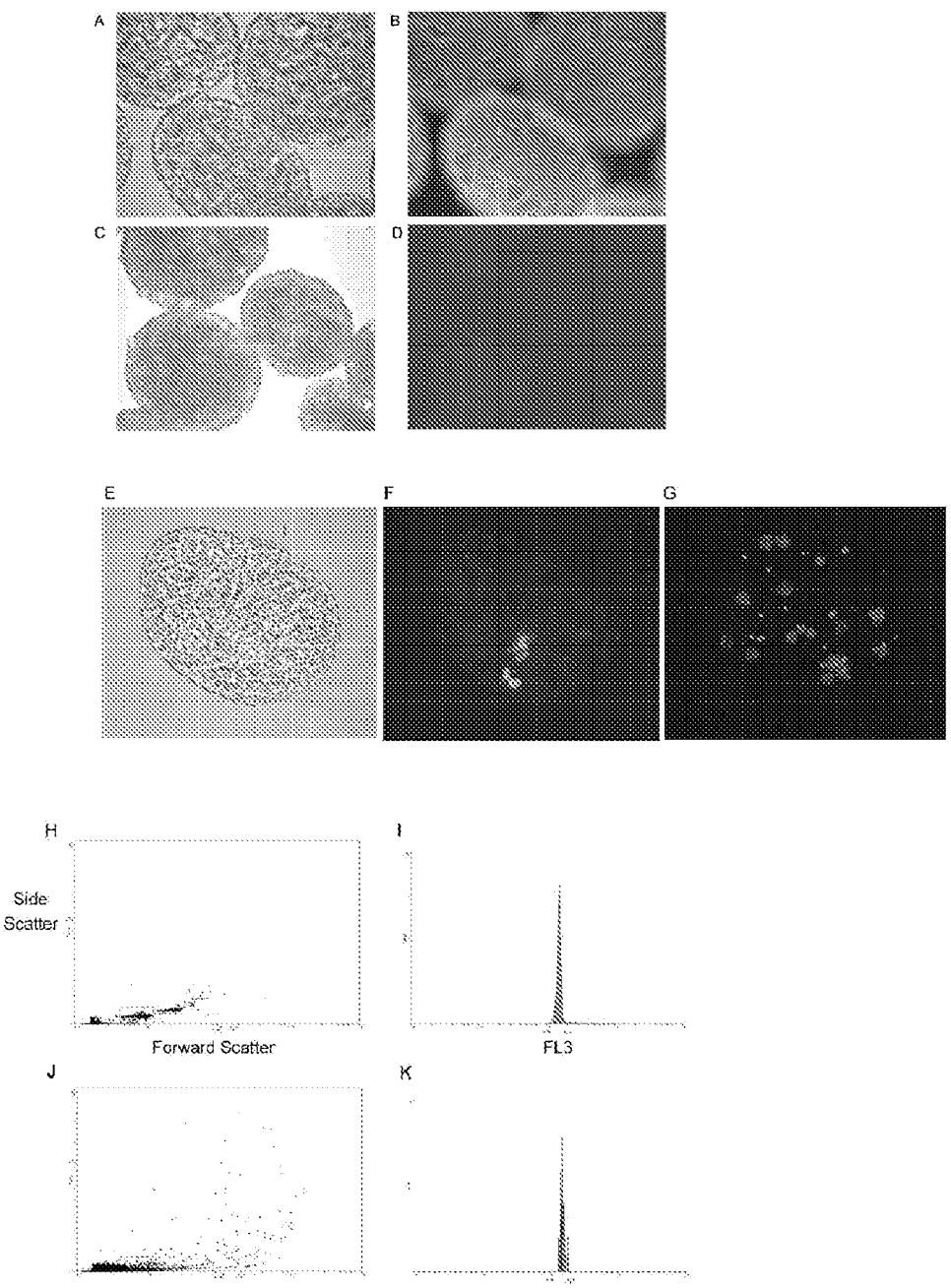

FIG. 16 shows data from the automated analysis of microcarriers and cell units using a COPAS Select (Union Biometrica Inc., Somerville, Mass.) instrument. Panels A and B: CYTODEX 3 microcarriers suspended in PBS were passed through the sorter and monitored for size (Time of Flight; TOF) versus optical scattering (Extinction; Ext) [A], and for green fluorescence (FLU1) versus red fluorescence (FLU2) [B]. Panels C and D: Analysis of CYTODEX 3 microcarriers labelled with red fluorescent latex beads showing a plot of Ext vs TOF [C], and fluorescence [D]; comparison of panels B and D illustrates that labelling of the microcarriers results in an increase in their red fluorescence signal. Panels E and F: Analysis of a group of cell units comprising CYTODEX 3 and ES cells expressing a Tau-GFP transgene. Increased scatter in the plot showing Ext vs TOF [E] and the broad range of green fluorescence (FLU1) [F] reveal cell units which can be sorted on the basis of cell number.

Figure 17:
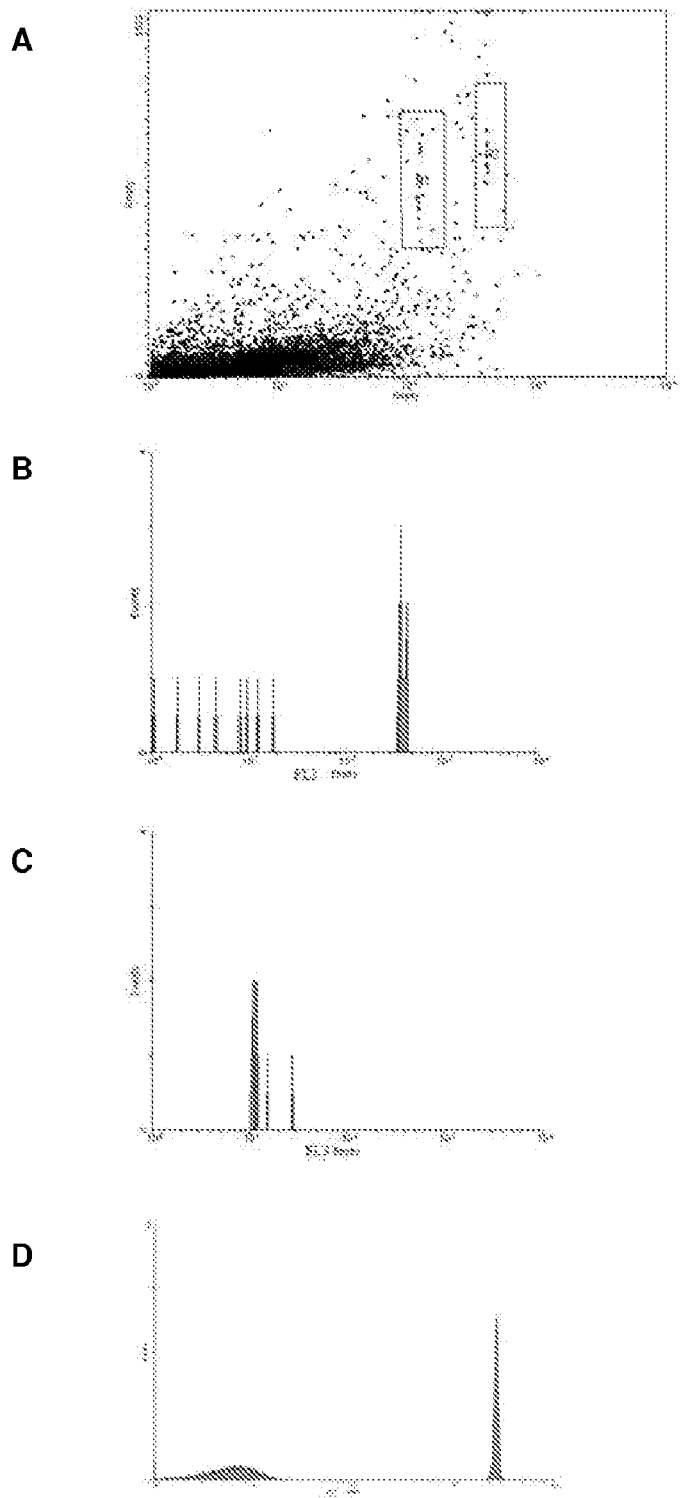

FIG. 17 shows identification of a tag used to label a cell unit. Panels A-D: Streptavidin-FITC labelling of Cultispher microcarriers modified with biotin (A, B) or in their native untreated state (C, D). Panels E-G: Cell units comprising ES cells expressing a Tau-GFP fusion protein and biotinylated Cultspher G microcarriers labelled with stretavidin-coated red-fluorescent, 1 µm latex beads (Sigma), observed under phase microscopy (E), and under green (F) and red (G) epifluorescence optics to visualise GFP-labelled cells and red fluorescent tags, respectively. Panels H-K: Calibration of FACS using a control sample of 1 µm red-fluorescent latex beads (Sigma) showing the characteristic forward and sidescatter parameters (H; boxed area) and the characteristic fluorescence intensity in the FL3 fluorescence channel (I). FACS analysis of a single proteolytically digested cell unit labelled with 1 µm red-fluorescent latex beads (Sigma), can be carried out by gating on the previously determined size parameters for the tags (J; boxed area) followed by detection of the characteristic FL3 channel intensity characteristic of the tags (K).

Figure 18:
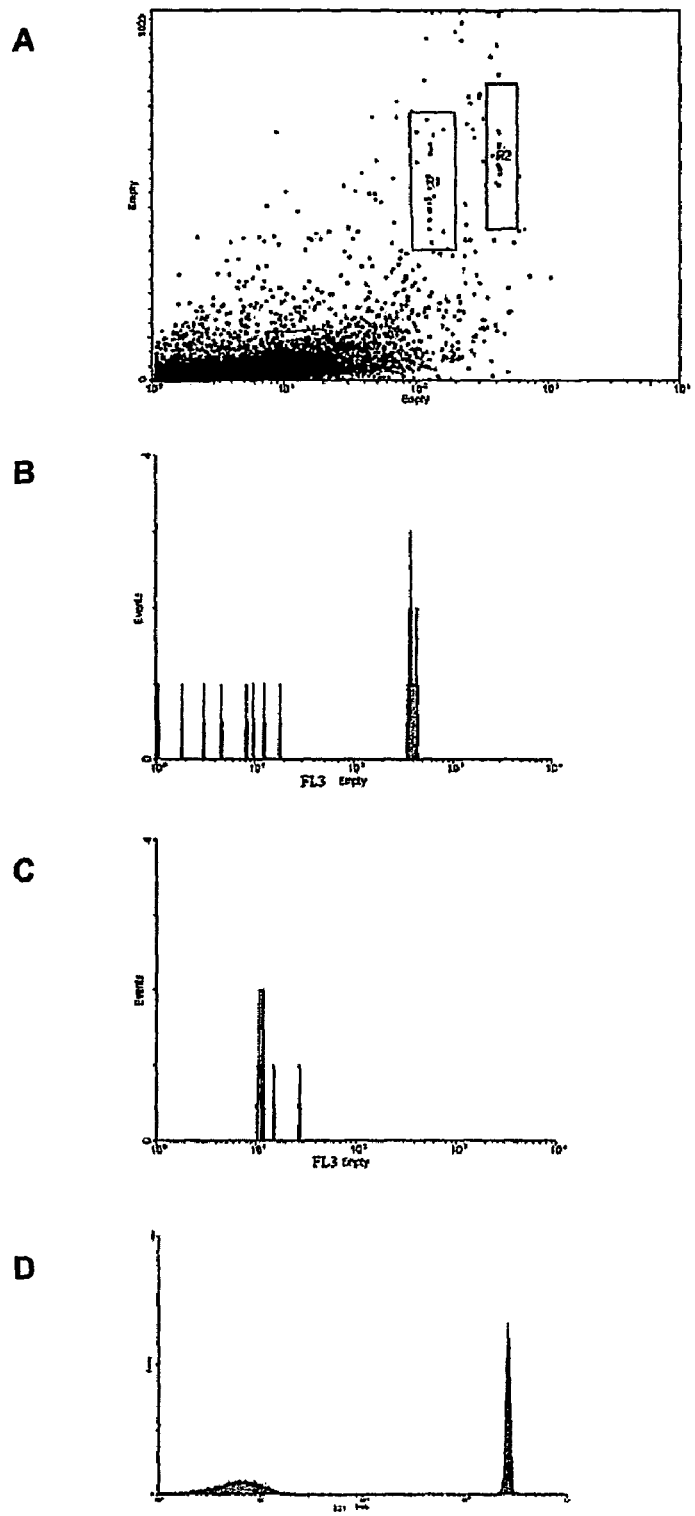

FIG. 18 shows identification of a multiplicity of tags used to label microcarriers. Panel A: Forward/side scatter parameters set with control tags were used to define size gates for 4.4 µm (Gate R1), 5.5 µm (Gate R2), and 1 µm (Gate R3) beads. Panels B-D: FACS analysis of a proteolytic digest of labelled microcarriers reveals the presence of tags corresponding to green fluorescent 4.4 µm bead set no. 5 from Bangs Labs (Panel B); green-fluorescent 5.5 µm bead set no. 1 from Bangs Labs (Panel C), and 1 µm red fluorescent beads from Sigma (Panel D).

DETAILED DESCRIPTION OF THE INVENTION

Definitions

Culture Conditions As used herein, the term "culture conditions" refers to the environment which cells are placed in or are exposed to in order to promote growth or differentiation of said cells. Thus, the term refers to the medium, temperature, atmospheric conditions, substrate, stirring conditions and the like which may affect the growth and/or differentiation of cells. More particularly, the term refers to specific agents which may be incorporated into culture media and which may influence the growth and/or differentiation of cells.

Cell A cell, as referred to herein, is defined as the smallest structural unit of an organism that is capable of independent functioning, or a single-celled organism, consisting of one or more nuclei, cytoplasm, and various organelles, all surrounded by a semipermeable cell membrane or cell wall. The cell may be prokaryotic, eukaryotic or archaebacterial. For example, the cell may be a eukaryotic cell. Mammalian cells are preferred, especially human cells. Cells may be natural or modified, such as by genetic manipulation or passaging in culture, to achieve desired properties. A stem cell is defined in more detail below, and is a totipotent, pluripotent or multipotent cell capable of giving rise to more than one differentiated cell type. Stem cells may be differentiated in vitro to give rise to differentiated cells, which may themselves be multipotent, or may be terminally differentiated. Cells differentiated in vitro are cells which have been created artificially by exposing stem cells to one or more agents which promote cell differentiation.

Cellular process A cellular process is any characteristic, function, process, event, cause or effect, intracellular or extracellular, which occurs or is observed or which can be attributed to a cell. Examples of cellular processes include, but are not limited to, viability, senescence, death, pluripotency, morphology, signalling, binding, recognition, molecule production or destruction (degradation), mutation, protein folding, transcription, translation, catalysis, synaptic transmission, vesicular transport, organelle function, cell cycle, metabolism, proliferation, division, differentiation, phenotype, genotype, gene expression, or the control of these processes.

Cell unit A group of cells, which may be a group of one. Pools of cell units may be sorted, subdivided and handled without substantially dissociating the cell units themselves, such that the cell unit behaves as a colony of cells and each cell in the cell unit is exposed to the same culture conditions. For example, a cell unit may comprise a bead to which is adhered a group of cells.

Totipotent A totipotent cell is a cell with the potential to differentiate into any type of somatic or germ cell found in the organism. Thus, any desired cell may be derived, by some means, from a totipotent cell.

Pluripotent A pluripotent cell is a cell which may differentiate into more than one, but not all, cell types.

Label A label or tag, as used herein, is a means to identify a cell unit and/or determine a culture condition, or a sequence of culture conditions, to which the cell unit has been exposed. Thus, a label may be a group of labels, each added at a specific culturing step; or a label added at the beginning or the experiment which is modified according to, or tracked during, the culturing steps to which the cell unit is exposed; or simply a positional reference, which allows the culturing steps used to be deduced. A label or tag may also be a device that reports or records the location or the identity of a cell unit at any one time, or assigns a unique identifier to the cell unit. Examples of labels or tags are molecules of unique sequence, structure or mass; or fluorescent molecules or objects such as beads; or radiofrequency and other transponders; or objects with unique markings or shapes.

Exposure to culture conditions A cell is exposed to culture conditions when it is placed in contact with a medium, or grown under conditions which affect one or more cellular process(es) such as the growth, differentiation, or metabolic state of the cell. Thus, if the culture conditions comprise culturing the cell in a medium, the cell is placed in the medium for a sufficient period of time for it to have an effect. Likewise, if the conditions are temperature conditions, the cells are cultured at the desired temperature.

Pooling The pooling of one or more groups of cell units involves the admixture of the groups to create a single group or pool which comprises cell units of more than one background, that is, that have been exposed to more than one different sets of culture conditions. A pool may be subdivided further into groups, either randomly or non-randomly; such groups are not themselves "pools" for the present purposes, but may themselves be pooled by combination, for example after exposure to different sets of culture conditions.

Proliferation Cell growth and cell proliferation are used interchangeably herein to denote multiplication of cell numbers without differentiation into different cell types or lineages. In other words, the terms denote increase of viable cell numbers. Preferably proliferation is not accompanied by appreciable changes in phenotype or genotype.

Differentiation Cell differentiation is the development, from a cell type, of a different cell type. For example, a bipotent, pluripotent or totipotent cell may differentiate into a neural cell. Differentiation may be accompanied by proliferation, or may be independent thereof. The term 'differentiation' generally refers to the acquisition of a phenotype of a mature cell type from a less developmentally defined cell type, e.g. a neuron, or a lymphocyte, but does not preclude transdifferentiation, whereby one mature cell type may convert to another mature cell type e.g. a neuron to a lymphocyte.

Differentiation state The differentiation state of a cell is the level to which a cell has differentiated along a particular pathway or lineage.

State of a cellular process The state of a cellular process refers to whether a cellular process is occurring or not and in complex cellular processes can denote a particular step or stage in that cellular process. For example, a cellular differentiation pathway in a cell may be inactive or may have been induced and may comprise a number of discrete steps or components such as signalling events characterised by the presence of a characteristic set of enzymes or intermediates.

Gene A gene is a nucleic acid which encodes a gene product, be it a polypeptide or an RNA gene product. As used herein, a gene includes at least the coding sequence which encodes the gene product; it may, optionally, include one or more regulatory regions necessary for the transcription and/ or translation of the coding sequence.

Gene Product A gene product is typically a protein encoded by a gene in the conventional manner. However, the term also encompasses non-polypeptide gene products, such as ribonucleic acids, which are encoded by the gene.

Nucleic acid synthesis Nucleic acids may be synthesised according to any available technique. Preferably, nucleic acid synthesis is automated. Moreover, nucleic acids may be produced by biological replication, such as by cloning and replication in bacterial or eukaryotic cells, according to procedures known in the art.

Differential Expression Genes which are expressed at different levels in response to cell culture conditions can be identified by gene expression analysis, such as on a gene array, by methods known in the art. Genes which are differentially expressed display a greater or lesser quantity of mRNA or gene product in the cell under the test conditions than under alternative conditions, relative to overall gene expression levels.

Transfection Genes may be transfected into cells by any appropriate means. The term is used herein to signify conventional transfection, for example using calcium phosphate, but also to include other techniques for transferring nucleic acids into a cell, including transformation, viral transduction, electroporation and the like.

Modulation The term modulation is used to signify an increase and/or decrease in the parameter being modulated. Thus, modulation of gene expression includes both increasing gene expression and decreasing gene expression.

Cell-Based Assays

Cell-based assays are an important part of modern biomedical sciences and comprise any assay that involves a step in which a cell is used. Cell-based assays can be used across nearly all stages of the pharmaceutical drug discovery and development process, and are valuable in providing information about how a compound is likely to interact in a biological system, not just about how it interacts with a potential drug target in isolation.

For example, cell-based assays can be used to identify and validate potential drug targets. Cell-based assays have been developed that can be used to identify genes or cellular pathways involved in disease processes, to determine the functions of target genes, or to measure phenotypic changes that may be induced upon activation of certain genes or their products.

Cell-based assays can also be used in drug discovery for lead-compound discovery, selection, and optimization. Unlike the biochemical assays that are often used in traditional high-throughput-screening assays, cell-based assays can provide information relating to drug properties such as absorption, permeability, selectivity, specificity, and metabolism. As a result, lead compounds that are selected after cell-based screening are better characterized, more likely to provide valuable leads and less likely to be eliminated in subsequent phases of the drug discovery process.

A major application of cell-based assays is in toxicity screening. A crucial part of drug discovery and development is the screening of drug candidates to eliminate compounds that will cause side effects. However, current methodologies are largely inadequate, and in particular the use of animal models for toxicity screening is expensive and time-consuming. In addition, animal models can be unreliable, because results in these models do not always accurately predict how a compound will perform in humans. Thus human cell-based screening is preferred.

Stem Cells

Stem cells are described in detail in Stem Cells: Scientific Progress and Future Research Directions. Department of Health and Human Services. June 2001.

Stem cells are cells that are capable of differentiating to form at least one and sometimes many specialised cell types. The repertoire of the different cells that can be formed from stem cells is thought to be exhaustive; that is to say it includes all the different cell types that make up the organism. Stem cells are present throughout the lifetime of an organism, from the early embryo where they are relatively abundant, to the adult where they are relatively rare. Stem cells present in many tissues of adult animals are important in normal tissue repair and homeostasis.

The existence of these cells has raised the possibility that they could provide a means of generating specialised functional cells that can be transplanted into humans and replace dead or non-functioning cells in diseased tissues. The list of diseases for which this may provide therapies includes Parkinson's disease, diabetes, spinal cord injury, stroke, chronic heart disease, end-stage kidney disease, liver failure and cancer. In order for cell replacement therapy to become feasible at least two major breakthroughs in stem cell research are required. First, conditions for growing stem cells to sufficient numbers need to be developed, so that therapeutically relevant doses of cells can be manufactured. Ideally large-scale cultures would be possible, providing material to treat multiple patients. Secondly, as undifferentiated stem cells transplanted into animals frequently give rise to tumours, it is envisaged that differentiating the stem cells into more specialised cells will be a pre-requisite for cell replacement therapy and it will thus be necessary to discover conditions for differentiating stem cells in to the particular, specialised cell types required for different diseases.

It is clear that the key to overcoming these obstacles lies in devising suitable methods of cell culture for stem cells and their derivatives. However, because of the reasons explained above—namely the laborious process of trial and error involved in the evolution of cell culture techniques—the task is particularly difficult. Hence one of the applications of the invention described herein is in the elucidation of techniques for the growth and differentiation of stem cells.

Types of Stem Cell

There is still considerable debate about what constitutes a stem cell, however for the purposes of this discussion a key characteristic is the ability to differentiate into a different cell type. Examples of stem cells are given below.

Different stem cells have differing potential to form various cell types: spermatogonial stem cells are unipotent as they naturally produce only spermatozoa, whereas haematopoietic stem cells are multipotent, and embryonic stem cells are thought to be able to give rise to all cell types and are said to be totipotent or pluripotent.

To date three types of mammalian pluripotent stem cell have been isolated. These cells can give rise to cell types that are normally derived from all three germ layers of the embryo (endoderm, mesoderm and ectoderm). The three types of stem cell are: embryonal carcinoma (EC) cells, derived from testicular tumours; embryonic stem (ES) cells, derived from the pre-implantation embryo (normally the blastocyst); and embryonic germ (EG) cells derived from the post-implantation embryo (normally cells of the foetus destined to become part of the gonads). These cells are receiving particular attention in the effort to direct differentiation, precisely because they are pluripotent.

Stem cells are also present in the adult organism. An adult stem cell is an undifferentiated cell that occurs in a differentiated (specialised) tissue, renews itself, and can differentiate to yield more specialised cells. Recently it has been shown that adult stem cells are capable of plasticity, that is to say they can differentiate to yield cell types that are not characteristic of the tissue in which they reside, nor indeed of the germ layer from which that tissue originates For example, it has been shown that blood stem cells (derived from mesoderm) can differentiate into neurons (normally derived from ectoderm). Toma et al. (2001, *Nature Cell Biol.* 3, p 778-784) have recently described the identification and isolation of a new type of stem cell that was derived from the dermis of the skin. These stem cells were termed skin-derived precursor (SKP) cells. The SKP cells could be induced to differentiate by culturing on poly-lysine and varying the concentration of serum in the culture medium. In the absence of serum they differentiate into neurons and glial cells; with addition of 3% serum they differentiate into smooth-muscle cells; and increasing the serum to 10% causes the SKP cells to differentiate into adipocytes. Adult stem cells have so far been reported in tissues as diverse as the nervous system, the bone marrow and blood, the liver, skeletal muscle, the skin and digestive system.

In addition to the adult stem cells there are numerous types of progenitor or precursor cells. These are cells that are partially restricted in their differentiative potential and occur in probably all of the tissues of the body—they are capable of differentiating but differ from stem cells in that their repertoire is not as broad, and by definition they are not capable of self-renewal.

Recent evidence even suggests that differentiated cell types are capable of changing phenotype. This phenomenon, termed transdifferentiation, is the conversion of one differentiated cell type to another, with or without an intervening cell division. It was previously generally accepted that the terminal differentiated state is fixed, but it is now clear that differentiation can sometimes be reversed or altered. In vitro protocols are now available in which cell lines can be induced to transdifferentiate (see Shen, Slack & Tosh, 2000, *Nature Cell Biol*. vol 2, p. 879-887; Horb et al, 2003, Current Biol. Vol 13, p 105-115). Finally, there have been reports of specialised cell types that can de-differentiate to yield stem-like cells with the potential to differentiate into further cell types.

Stem Cell Growth and Differentiation

An important property of stem cells is their ability to divide symmetrically in culture, giving rise to two daughter cells that are exact copies of the stem cell from which they were derived. This allows stem cells to be expanded in culture in their undifferentiated state, producing enough material for biological studies or even cell therapy. The means by which stem cells are able to do this is understandably the subject of intensive research, yet few of the factors that promote stem cell renewal are known. Typically, pluripotent stem cell lines are maintained on mitotically inactive feeder layers of fibroblasts, or medium conditioned by such cells. It is assumed that feeder cells remove/neutralise some unknown factor from the culture medium, and/or they provide a factor that suppresses the differentiation and promotes the self-renewal of stem cells. One such factor is leukaemia inhibitory factor (LIF), a member of the cytokine family related to IL-6, which is capable of promoting mouse ES cell self-renewal in the absence of feeder cells. Stem cells grown in the absence of feeder cells (and/or LIF) often differentiate spontaneously and haphazardly, producing a mixture of differentiated cell types.

The factors that influence stem cell self-renewal may either be stimulatory or inhibitory and may function extracellularly or intracellularly. In the case of the secreted factor LIF, it is known that its extracellular receptor is gp 130, and that activation of this protein is sufficient for inhibiting murine ES cell differentiation. Within the cell, a crucial downstream effector of gp130 is the signal transducer and activator of transcription-3 (STAT-3). Another molecule which is particularly important in maintaining stem cell pluripotency is the transcription factor Oct-4, which when downregulated artificially leads to the loss of the pluripotent state in ES cells or mice. Other signalling molecules that naturally inhibit ES cell self-renewal, such as the mitogen-activated protein kinases, have also been elucidated. A major goal of stem cell research will be the discovery of natural and synthetic factors, drugs, polypeptides, genes, oligonucleotides, tissue culture media and conditions, specific conditioned media, feeder cells, and other stimuli that have the effect of promoting the expansion and retaining the differentiation potential of various types of stem cell. This includes adult stem cells, which at present have not been expanded appreciably in cell culture.

The second great challenge of stem cell research is to direct the differentiation of stem cells to particular cell types which are functional, can replace cells lost in various disease states, and result in a positive clinical outcome. Coaxing stem cells to begin differentiating is actually a fairly straightforward process. For instance, ES cells removed from feeder cultures and grown to confluence on an adherent substrate will begin to differentiate spontaneously. Similarly, ES cells removed from feeder cultures and grown on a non-adherent substrate will form embryoid bodies—clusters of undifferentiated and partially differentiated cells from all three germ layers. These cells can be subsequently dissociated and plated in monolayer culture, and exposed to factors that promote directed differentiation. Cultures exposed to these factors are more likely to be populated by fewer types of differentiated cell, compared to embryoid bodies or untreated cultures of differentiating cells which comprise mixtures of many different cell types. Nevertheless, few if any conditions have been devised thus far that produce substantially pure cultures of differentiated cells. In addition it is not clear if any of the protocols devised for stem cell differentiation yield cells that are suitable for cell replacement therapy—it may be that the cells have not terminally differentiated into the precise phenotype required, or that the differentiated cells are no longer viable in vivo.

The factors that have been used to induce directed differentiation of stem cells include: retinoic acid, epidermal growth factor (EGF), bone morphogenic proteins (BMPs), basic fibroblast growth factor (bFGF), activin-A, transforming growth factor beta-1 (TFG β-1), hepatocyte growth factor, nerve growth factor, sonic hedgehog (SHH), interleukin-3 (IL-3), interleukin-6 (IL-6), granulocyte macrophage colony stimulating factor (GM-CSF), erythropoietin, vitamin D3, dexamethasone, β-mercaptoethanol, butylated hydroxyanisole, 5-azacytidine, DMSO, insulin, thyroid hormone (T3), LIF, foetal calf serum, vascular endothelial growth factor (VEGF), steel factor, variations in oxygen concentration, ascorbic acid, β-glycerophosphate, nicotinamide, platelet derived growth factor (PDGF), CAMP, various cell adhesion molecules and substrates, and others. In addition to these defined factors, it is likely that undefined extracts, such as conditioned media, human and animal tissue homogenates, or plant extracts can be used to direct stem cell differentiation. Progressive fractionation of these undefined extracts may yield active fractions or even pure components with high potency. These factors can be added to the growth medium used in a particular experiment, either alone, or in combination, or in a defined order which is crucial to the experimental result.

Many systems that have been devised for the differentiation of stem cells in vitro are complex multi-stage procedures, in which the precise nature of the various steps, as well as the chronology of the various steps, are important. For instance, Lee et al (2000, Nature Biotechnology, vol. 18, p 675-679) used a five stage protocol to derive dopaminergic neurons from mouse ES cells: 1) undifferentiated ES cells were expanded on gelatin-coated tissue culture surface in ES cell medium in the presence of LIF; 2) embryoid bodies were generated in suspension cultures for 4 days in ES cell medium; 3) nestin-positive cells were selected from embryoid bodies in ITSFn medium for 8 days after plating on tissue culture surface; 4) nestin-positive cells were expanded for 6 days in N2 medium containing bFGF/laminin; 5) finally the expanded neuronal precursor cells were induced to differentiate by withdrawing bFGF from N2 medium containing laminin.

In a second example of serial cell culture, Bonner-Weir et al. [Proc. Natl. Acad. Sci. (2000) 97: 7999-8004] derived insulin producing cells from human pancreatic ductal cells by: 1) selecting ductal cells over islet cells by selective adhesion on a solid surface in the presence of serum for 24 days; 2) subsequently withdrawing serum and adding keratinocyte growth factor to select for ductal epithelial cells over fibroblasts for 5-10 days; and 3) overlaying the cells with the extracellular matrix preparation 'Matrigel' for 3-6 weeks.

In a further example of serial cell culture, Lumelsky et al. [Science (2001) 292: 1389-1394] derived insulin secreting cells by directed differentiation of mouse embryonic stem (ES) cells by: 1) expanding ES cells in the presence of LIF for 2-3 days; 2) generating embryoid bodies in the absence of LIF over 4 days; 3) selecting nestin-positive cells using ITSFn medium for 6-7 days; 4) expanding pancreatic endocrine precursors in N2 medium containing B27 media supplement and bFGF for 6 days; and 5) inducing differentiation to insulin secreting cells by withdrawing bFGF and adding nicotinamide.

However it is not only the sequence and duration of the various steps or the series of addition of different factors that is important in the determination of cell differentiation. As embryonic development is regulated by the action of gradients of signalling factors that impart positional information, it is to be expected that the concentration of a single signalling factor, and also the relative concentration of two or more factors, will be important in specifying the fate of a cell population in vitro and in vivo. Factor concentrations vary during development and stem cells respond differently to different concentrations of the same molecule. For instance, stem cells isolated from the CNS of late stage embryos respond differently to different concentrations of EGF: low concentrations of EGF result in a signal to proliferate, while higher concentrations of EGF result in proliferation and differentiation to astrocytes.

Many of the factors that have been found to influence self-renewal and differentiation of stem cells in vitro are naturally-occurring molecules. This is to be expected, as differentiation is induced and controlled by signalling molecules and receptors that act along signal transduction pathways. However, by the same token, it is likely that many synthetic compounds will have an effect on stem cell differentiation. Such synthetic compounds that have high probability of interacting with cellular targets within signalling and signal transduction pathways (so called drugable targets) are routinely synthesised, for instance for drug screening by pharmaceutical companies. Once known, these compounds can be used to direct the differentiation of stem cells ex vivo, or can be administered in vivo in which case they would act on resident stem cells in the target organ of a patient.

Common Variables in Tissue Culture

In developing conditions for the successful culture of a particular cell type, or in order to achieve or modulate a cellular process, it is often important to consider a variety of factors.

One important factor is the decision of whether to propagate the cells in suspension or as a monolayer attached to a substrate. Most cells prefer to adhere to a substrate although some, including transformed cells, haematopoletic cells, and cells from ascites, can be propagated in suspension.

Assuming the culture is of adherent cells, an important factor is the choice of adhesion substrate. Most laboratories use disposable plastics as substrates for tissue culture. The plastics that have been used include polystyrene (the most common type), polyethylene, polycarbonate, Perspex, PVC, Teflon, cellophane and cellulose acetate. It is likely that any plastic can be used, but many of these will need to be treated to make them wettable and suitable for cell attachment. Furthermore it is very likely that any suitably prepared solid substrate can be used to provide a support for cells, and the substrates that have been used to date include glass (e.g. alum-borosilicate and soda-lime glasses), rubber, synthetic fibres, polymerised dextrans, metal (e.g. stainless steel and titanium) and others.

Some cell types, such as bronchial epithelium, vascular endothelium, skeletal muscle and neurons require the growth substrate to be coated with biological products, usually extracellular matrix materials such as fibronectin, collagen, laminin, polylysine or others. The growth substrate and the method of application (wet or dry coating, or gelling) can have an effect on cellular processes such as the growth and differentiation characteristics of cells, and these must be determined empirically as discussed above.

Probably the most obviously important of the variables in cell culture is the choice of culture medium and supplements such as serum. These provide an aqueous compartment for cell growth, complete with nutrients and various factors, some of which have been listed above, others of which are poorly defined. Some of these factors are essential for adhesion, others for conveying information (e.g. hormones, mitogens, cytokines) and others as detoxificants. Commonly used media include RPMI 1640, MEM/Hank's salts, MEM/Earie's salts, F12, DMEM/F12, L15, MCDB 153, and others. The various media can differ widely in their constituents—some of the common differences include sodium bicarbonate concentration, concentration of divalent ions such as Ca and Mg, buffer composition, antibiotics, trace elements, nucleosides, polypeptides, synthetic compounds, drugs, etc. It is well known that different media are selective, meaning they promote the growth of only some cell types. Media supplements such as serum, pituitary brain and other extracts, are often essential for the growth of cells in culture, and in addition are frequently responsible for determining the phenotype of cells in culture, i.e. they are capable of determining cell survival or directing differentiation. The role of supplements in cell processes such as differentiation is complex and depends on their concentration, the time point at which they are added to the culture, the cell type and medium used. The undefined nature of these supplements, and their potential to affect the cell phenotype, have motivated the development of serum-free media. As with all media, their development has come about largely by trial and error, as has been discussed above.

The gas phase of the tissue culture is also important and its composition and volume which should be used can depend on the type of medium used, the amount of buffering required, whether the culture vessel is open or sealed, and whether a particular cellular process needs to be modulated. Common variables include concentration of carbon dioxide and oxygen.

Other conditions important to tissue culture include the choice of culture vessel, amount of headspace, inoculation density, temperature, frequency of media changes, treatment with enzymes, rate and mode of agitation or stirring.

Varying the cell culture conditions is therefore a method of achieving a desired cellular process. One aspect of the invention recognises that variation of the cell culture conditions in a serial manner can be a highly effective method for achieving a cellular effect. In various applications, for instance in studies of cell differentiation, it will often be the case that a specific series of different tissue culture conditions are required to effect a cellular process. The different conditions may include additions or withdrawals to/from the media or the change of media at specific time points. Such a set of conditions, examples of which are given below, are commonly developed by trial end error as has been discussed above.

Formation of Cell Units

An important aspect of the present invention is that groups of cells (cell colonies) can be grown in cell culture under various conditions and that the colony can largely maintain its integrity under various conditions, when disturbed, and when mixed with other colonies. Such groups or colonies are referred to herein as cell units. Formation of cell units may be achieved, by way of illustration, by growing cells as adherent cultures on solid substrates such as carriers. If cell proliferation occurs after seeding on the carriers, the daughter cells will attach on the same carrier and form part of the same colony. In general, live adherent cells do not readily dissociate from their growth substrate, and so the integrity of the cell colony persists despite any mechanical manipulation of the carrier, agitation of the culture medium, or transfer into another tissue culture system.

Similarly, if at any time multiple carriers are placed in the same vessel (e.g. beads are pooled) then there will be no substantial transfer of cells from one bead to another.

One advantage of growing cells in units or colonies is that if a unit is placed serially in a set of different tissue culture media, then all the cells comprising the colony will have been exposed to the same series of culture conditions, in the same order and for the same period of time. Growing cells in units that are not necessarily themselves adherent to the tissue culture vessel has the advantage that individual colonies can be removed at will and transferred to a different culture vessel. One of the advantages of this method is that tissue culture can be miniaturised: relatively few cells are required to colonise a microcarrier bead (see below) compared to even the smallest tissue culture flask. A further advantage of growing cell units formed on carriers is that cell culture can be scaled up. Growth of stem cells on carriers offers a way of scaling up production to provide enough material for stem cell therapy. Equally, differentiation of stem cells on carriers offers a way of scaling up production as differentiation proceeds, eventually providing enough material for cell replacement therapies. Scale up of such cell cultures requires at least 50 g (dry weight) of microcarrier, preferably, 100 g, 500 g, 1 kg, 10 kg or more.

Another important advantage of forming cell units on solid substrates is that the substrate—and therefore the attached cells by reason of association—can be labelled by various means.

Glass spheres of 3 mm and 5 mm have been widely used as cell adhesion substrates, particularly in glass bead bioreactors (e.g. such as manufactured by Meredos Gmbh) used for the scale-up of cell cultures. These beads are typically used in packed beds rather than batch culture, to avoid mechanical damage to the adherent cells.

In contrast, when cells are grown on smaller carriers they can be treated as a suspension culture. A common method of growing cells on small carriers is referred to as microcarrier cell culture (see 'Microcarrier cell culture, Principles and Methods', Edition AA, available from Amersham Biosciences (18-1140-62); herein incorporated in its entirety by reference). Microcarrier cultures are used commercially for antibody and interferon production in fermenters of up to 4000 liters. A variety of microcarriers is available, ranging in shape and size and made of different materials. Microcarrier beads made of polystyrene (BIOSILON, Nunc), glass (BIOGLASS, Solohill Eng), collagen (BIOSPHERES, Solohill Eng), DEAE sephadex (CYTODEX-1, Pharmacia), dextran (DORMACELL, Pfeifer & Langen), cellulose (DE-53, Whatman), gelatin (GELIBEAD, Hazelton Lab), and DEAE dextran (MICRODEX, Dextran Prod.) amongst others are commercially available. These carriers are well characterised in terms of the specific gravity of the beads, the diameter and the surface area available for cell growth. In addition a number of porous (micro) carriers are available with greatly increased surface area for cell growth. A further characteristic of these porous carriers is that they are suitable for growth of both anchorage dependent cells, as well as for suspension cells which are carried by entrapment in the network of open, interconnecting pores. Porous carriers are available in materials such as gelatin (CULTISPHER G, HyClone), cellulose (CYTOCELL, Pharmacia), polyethylyne (CYTOLINE 1 and 2, Pharmacia), silicone rubber (IMMOBASIL, Ashby Scientific), collagen (MICROSPHERE, Cellex Biosciences), and glass (SIRAN, Schott Glassware). These carriers are variously suited to stirred, fluidised or fixed bed culture systems.

As the physical properties of carriers are well known it is easy to calculate the number of carriers used in an experiment. Some of the carriers described and many besides are available as dried products which can be accurately weighed, and subsequently prepared by swelling in liquid medium. In addition the number of cells used to inoculate a microcarrier culture can be worked out and varied. For instance, a culture of CYTODEX 3 (2 g/liter) inoculated at 6 cells per bead will give a culture containing 8 million microcarriers, on which 48 million cells/liter are grown at a density of $5\times10^4$ cells/cm$^2$.

Harvesting of cells grown on microcarriers, or liberation of labels from microcarriers (see below), can be achieved by enzymatic detachment of cells, and/or by digestion of the carrier where applicable: gelatin carriers can be solubilised by trypsin and/or EDTA, collagen carriers using collagenase and dextran carriers using dextranase.

In addition to solid or porous microcarriers, cells may be grouped by immurement, i.e. confined within a medium permeable barrier. Membrane culture systems have been developed where a permeable dialysis membrane retains a group of cells, but allows the culture medium and its constituents to exchange freely with the inner and outer compartments. Cell culture in hollow fibre cartridges has also been developed, and a multitude of fibres and even turn-key systems are commercially available (e.g. from Amicon, Cellex Biosciences). Cell encapsulation in semi-solid matrices has also been developed, where cells are immobilised by adsorption, covalent bonding, crosslinking or entrapment in a polymeric matrix. Materials that have been used include gelatin, polylysine, alginate and agarose. A typical protocol, is to mix 5% agarose at 40° C. with a suspension of cells in their normal growth medium, to emulsify the mixture using an equal volume of paraffin oil and to cool in an ice bath, producing spheres of 80-200 µm diameter. These spheres can be separated from the oil and transferred to medium in a tissue culture vessel.

Cell entrapment is a simple method for the immobilisation of groups of cells, akin to the use of microcarriers or porous substrates. A simple technique is to enmesh cells in cellulose fibres such as DEAE, TLC, QAE, TEAE (all available from Sigma). Other more sophisticated devices are ceramic cartridges which are suitable for suspension cells, as in the OPTICEL culture system (Cellex Biosciences).

One skilled in the art will envisage, in addition to the above methods of creating cell units, other methods of creating groupings of cells including forming 3D cultures of cells such as neural spheres or embryoid bodies, or using tissues and indeed whole organisms such as *Drosophila* or *C. elegans*.

Cell units, or the substrates of which they are comprised, can be associated with a particular factor including, but without limitation, proteins, nucleic acids or other chemicals such as drugs. Pre-conditioning of substrates can be achieved in many ways, for instance simply by incubating the substrate with the factor of interest, or by attaching the factor covalently or non-covalently to the substrate. Soluble factors can be incorporated into dry materials by impregnation. This technique relies on the rapid ingress of liquid, carrying soluble factors, into dry porous material that concomitantly becomes swollen and ready for use. Solid factors can be incorporated for example by mixing the factor in fibrinogen with thrombin solution, at which point a fibrin clot containing the factor is formed. Multiple other ways can be envisaged of associating factor(s) with a cell group, in addition to impregnating, entrapping or encapsulating the factor together with cells.

A method for associating a cell group with a number of different factors is to pre-form cocktails of factors which are subsequently associated with a particular cell group. A second method would be to serially condition cell groups in a number of factors. Using dry formulations of cell group growth substrates as an example, this method would involve firstly partially swelling the substrate in a solution containing a first factor and subsequently further swelling the same in a solution containing a second factor, resulting in a substrate to which both factors have become associated. By devising a systematic protocol of associating cell groups with different combinations of different factors it will be possible to sample the effect on the cell group of any combination of a set of factors.

Regardless of the method used to condition cell units with factors, the factors are taken up by cells that comprise that cell unit. Factors leaking into the growth medium are diluted to such an extent that their concentration falls below physiologically relevant limits and they have no effect on any additional cell group to which they are exposed. The diffusion of the factor out of e.g. the substrate forming part of the cell unit is governed by parameters such as the nature and dimensions of the material, the mean pore diameter, and the molecular weight and concentration of the factor. To calibrate the process if necessary, factor release can be measured by physical assays such as HPLC analysis or release of labelled factor into the medium, or by biological assays such as the dorsal root ganglion outgrowth bioassay for neurotrophic factors.

Combinatorial Serial Culture of Cells

Split-Pool Cell Culture

Figure 1:
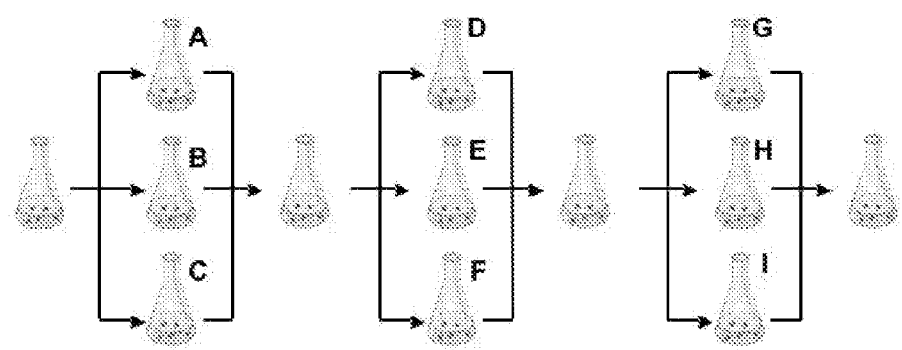
FIG. 1 shows an example of split-pool cell culture performed over three rounds. A group of cell units is obtained by growing under a given condition. Cell units are depicted as spheres and groups of cell units are shown in flasks. The cell units are split into three aliquots which are cultured for two days under different growth conditions denoted A, B, C. The cell units are subsequently pooled and split once more into three aliquots which are grown under conditions D, E or F. After two rounds of this protocol, it can be seen that the various cell groups have been exposed to all possible combinations of cell culture conditions.
Figure 2:
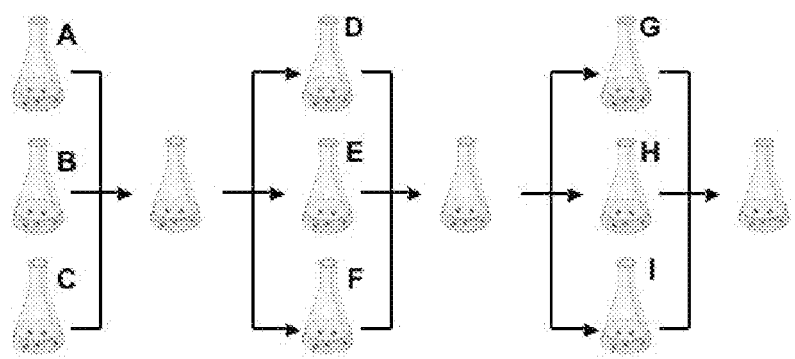
FIG. 2 shows a further example of split-pool cell culture. In this case the experiment begins with three groups A, B and C. The samples are pooled in the first step, and subsequently split into groups D, E and F.
Figure 3:
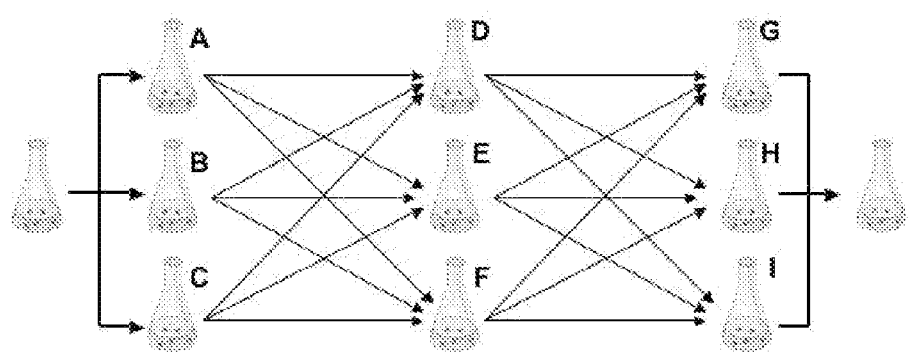
FIG. 3 shows a variation of the split-pool method where samples from groups A, B and C are directly partitioned into groups D, E and F without prior pooling. The partitioning of individual cell groups may be random, or may be predetermined.
Figure 4:
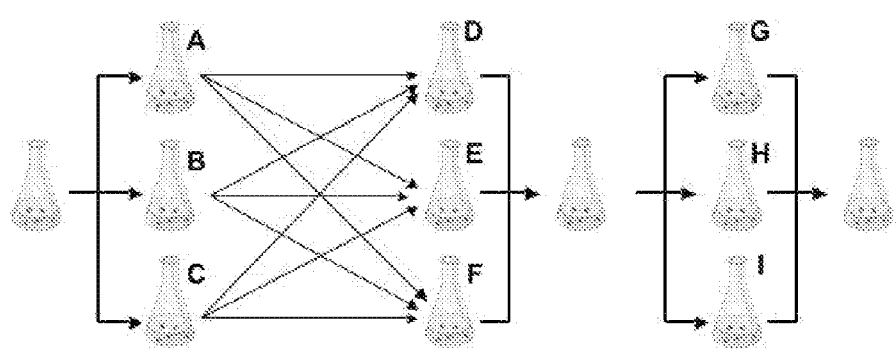
FIG. 4 shows a further variation of the split-pool method in which cell groups A, B and C are partitioned into cell groups D, E and F without prior pooling, whereas in a second step cell groups D, E and F and pooled and subsequently partitioned into cell groups G, H and I.

Forming cell units (particularly microscopic cell units) is furthermore useful for sampling multiple tissue culture conditions as each cell unit constitutes an easily handled unit that can be exposed to a variety of cell culture conditions. For simplicity, in this discussion we will assume that cell groupings are produced by growing cells in microcarrier culture, and the terms cell unit, cell group, colony and bead are used interchangeably. However, the methods described are equally applicable to any cell unit, for instance those described above. A particularly efficient method for sampling a large number of cell culture conditions is referred to as Combinatorial Cell Culture or split-pool cell culture (FIGS. 1 and 2) and In one embodiment involves the serial subdividing and combining of groups of cell units in order to sample multiple combinations of cell culture conditions. In one aspect of the invention the method operates by taking an initial starter culture (or different starter cultures) of cell units divided into $X_1$ number of aliquots each containing multiple beads (groups/colonies/carriers) which are grown separately under different culture conditions. Following cell culture for a given time, the cell units can be pooled by combining and mixing the beads from the different aliquots. This pool can be split again into $X_2$ number of aliquots, each of which is cultured under different conditions for a period of time, and subsequently also pooled. This iterative procedure of splitting, culturing and pooling (or pooling, splitting and culturing; depending on where one enters the cycle) cell units allows systematic sampling of many different combinations of cell culture conditions. The complexity of the experiment, or in other words the number of different combinations of cell culture conditions tested, is equal to the product of the number of different conditions $(X_1 \times X_2 \times \ldots X_n)$ sampled at each round. Note that the step of pooling all the cell units prior to a subsequent split can be optional—a step in which a limited number of cell units are pooled can have the same effect, as is illustrated in FIGS. 3 and 4. The invention therefore embodies a number of related methods of systematically sampling multiple combinations of cell culture conditions where groups of cell units are handled in bulk.

Regardless of the precise manner in which a diversity of cell culture conditions is sampled by this means the procedure is efficient because multiple cell units can share a single vessel, where they are cultured under identical conditions, and it can be carried out using only a few culture vessels at any one time (the number of culture vessels in use is equal to the number of split samples). In many respects the principle of this procedure resembles that of split synthesis of large chemical libraries (known as combinatorial chemistry), which samples all possible combinations of linkage between chemical building block groups (see for example: Combinatorial Chemistry, Oxford University Press (2000), Hicham Fenniri (Editor)). Split-pool cell culture can be repeated over any number of rounds, and any number of conditions can be sampled at each round. So long as the number of cell units (or colonised beads in this example) is greater than or equal to the number of different conditions sampled over all rounds, and assuming that the splitting of cell units occurs totally randomly, it is expected that there will be at least one cell unit that has been cultured according to each of the various combinations of culture conditions sampled by the experiment. This procedure can be used to sample growth or differentiation conditions for any cell type, or the efficiency of biomolecule production (e.g. production of erythropoietin or interferon) by any cell type. Because the procedure is iterative, it is ideally suited to testing multistep tissue culture protocols—for instance those described above in connection with stem cell differentiation. The variables which can be sampled using this technique include cell type, cell grouping (e.g. microcarrier culture, cell encapsulation, whole organism), growth substrate (e.g. fibronectin on microcarrier), duration of cell culture round, temperature, different culture media (including different concentrations of constituents), growth factors, conditioned media, co-culture with various cell types (e.g. feeder cells), animal or plant extracts, drugs, other synthetic chemicals, infection with viruses (incl. transgenic viruses), addition of transgenes, addition of antisense or anti-gene molecules (e.g. RNAi, triple helix), sensory inputs (in the case of organisms), electrical, light, or red-ox stimuli and others.

Split-Split Cell Culture

Figure 5:
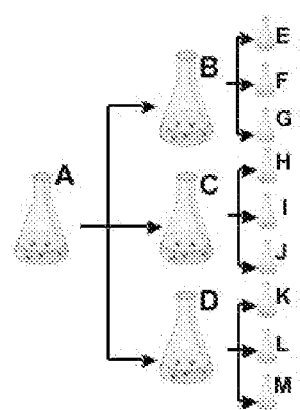
FIG. 5 shows a split-split protocol comprising a first step in which cell group A is split to form cell groups B, C and D, and a second step in which cell groups B, C and D are split to form cell groups E-M.
Figure 6:
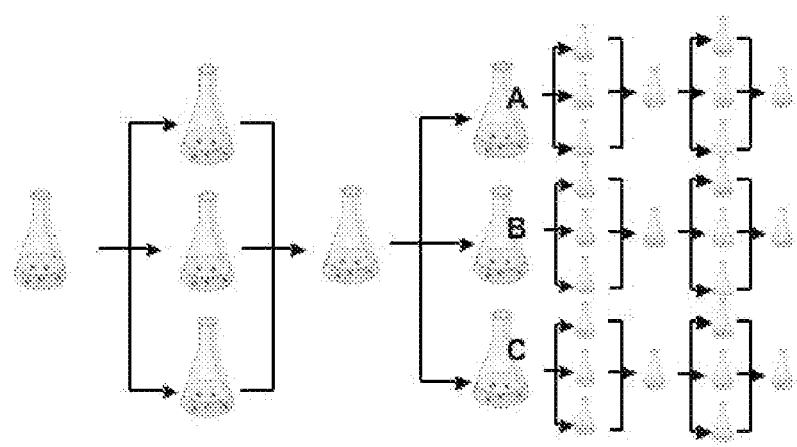
FIG. 6 shows a split-pool protocol which contains a split-split step. After two rounds of splitting and pooling, cell groups A, B and C are split without prior pooling, resulting in three cell group lineages variously derived from cell groups A, B or C. Note that including a split-split step can be used to deduce the role of cell culture conditions in producing a cellular effect. For example, if a cellular effect is observed in cell units derived from lineage A only, and assuming the cell culture conditions assayed in the various cell groupings subsequent to the divergence of lineages A, B and C are identical, then the conditions of culture of cell group A at the branching point must be essential to the cellular effect. Note also that the methods illustrated in FIGS. 1-6 can be used in a number of combinations.

The purpose of performing split-pool processes on cell units is to systematically expose these to a pre-defined combination of conditions. The person skilled in the art will conceive of many different means of achieving this outcome. In addition to split-pool processes and variations thereof, it is worthwhile briefly discussing split-split processes. A split-split process involves subdividing a group of cell units at least twice, without intervening pooling of cell units (FIG. 5). If split-split processes are used over a large number of rounds, the number of separate samples that are generated increases exponentially. In this case it is important to employ some level of automation, for example the use of a robotic platform and sophisticated sample tracking systems. The advantage of split-split steps is that (since cell units are not combined) it is possible to segregate lineages of the various cell units based on their cell culture history. Consequently split-split steps can be used to deduce if a particular cell culture condition is responsible for any given cellular process and therefore used to deduce the culture history of cell units (illustrated in FIG. 6, and explained in detail under 'Determination of culture history of a cell unit').

Predetermined Protocols

The splitting and/or pooling of cell units may be accomplished totally randomly or may follow a predetermined protocol. Where cell units are split and/or pooled randomly, the segregation of a given cell unit into any group is not predetermined or prejudiced in any way. In order to result in a high probability that at least one cell unit has been exposed to each of the possible combinations of cell culture conditions, it is advantageous to employ a larger number of cell units than the total number of combinations of cell culture conditions that are being tested. Under certain circumstances it is therefore advantageous to split and/or pool cell units according to a predetermined protocol, the overall effect being that adventitious duplications or omissions of combinations are prevented. Predetermined handling of cell units can be optionally planned in advance and logged on a spreadsheet or computer programme, and splitting and/or pooling operations executed using automated protocols, for instance robotics. Labelling of cell units (see below) can be by any of a number of means, for instance labelling by RFID, optical tagging or spatial encoding. Robotic devices capable of determining the identity of a sample, and therefore partitioning the samples according to a predetermined protocol, have been described (see 'Combinatorial Chemistry, A practical Approach', Oxford University Press (2000), Ed H. Fenniri). Alternatively, standard laboratory liquid handling and/or tissue culture robotics (for example such as manufactured by: Beckman Coulter Inc, Fullerton, Calif.; The Automation Partnership, Royston, UK) is capable of spatially encoding the identity of multiple samples and of adding, removing or translocating these according to pre-programmed protocols.

Analysis and/or Separation of Cell Units

Following each round of cell culture, or after a defined number of rounds, the cell units can be studied to observe any given cellular process that may have been affected by the tissue culture conditions. The examples below are illustrative and not intended to limit the scope of the invention.

Following each round of cell culture, or after a defined number of rounds, the cell units can be assayed to determine whether there are members displaying increased cell proliferation. This can be achieved by a variety of techniques, for instance by visual inspection of the cell units under a microscope, or by quantitating a marker product characteristic of the cell. This may be an endogenous marker such as a particular DNA sequence, or a cell protein which can be detected by a ligand or antibody. Alternatively an exogenous marker, such as green fluorescent protein (GFP), can be introduced into the cell units being assayed to provide a specific readout of (living) cells. Live cells can be visualised using a variety of vital stains, or conversely dead cells can be labelled using a variety of methods, for instance using propidium iodide. Furthermore the labelled cell units can be separated from unlabelled ones by a variety of techniques, both manual and automated, including affinity purification ('panning'), or by fluorescence activated cell sorting (FACS) or broadly similar techniques (FIG. 16). Depending on the application it may be possible to use standard laboratory equipment, or it may be advantageous to use specialised instrumentation. For instance, certain analysis and sorting instruments (e.g. see Union Biometrica Inc., Somerville Mass., USA) have flow cell diameters of up to one millimeter, which allows flow sorting of beads with diameters up to 500 microns. These instruments provide a reading of bead size and optical density as well as two fluorescent emission wavelengths from tags such as GFP, YFP or DS-red. Sorting speeds of 180,000 beads per hour and dispensing into multi-well plates or into a bulk receptor are possible.

Following each round of cell culture, or after a defined number of rounds, the cell units can be assayed to determine whether there are members displaying a particular genotype or phenotype. Genotype determination can be carried out using well known techniques such as the polymerase chain reaction (PCR), fluorescence in situ hybridization (FISH), DNA sequencing, and others. Phenotype determination can be carried out by a variety of techniques, for instance by visual inspection of the cell units under a microscope, or by detecting a marker product characteristic of the cell. This may be an endogenous marker such as a particular DNA or RNA sequence, or a cell protein which can be detected by a ligand, conversion of an enzyme substrate, or antibody that recognises a particular phenotypic marker (For instance see Appendix E of *Stem Cells: Scientific Progress and Future Research Directions*. Department of Health and Human Services. June 2001; appendices incorporated herein by reference). A genetic marker may also be exogenous, i.e. one that has been Introduced into the cell population, for example by transfection or viral transduction. Examples of exogenous markers are the fluorescent proteins (e.g. GFP) or cell surface antigens which are not normally expressed in a particular cell lineage or which are epitope-modified, or from a different species. A transgene or exogenous marker gene with associated transcriptional control elements can be expressed in a manner that reflects a pattern representative of an endogenous gene(s). This can be achieved by associating the gene with a minimal cell type-specific promoter, or by integrating the transgene into a particular locus (e.g. see European patent No. EP 0695351). The labelled cell units can be separated from unlabelled ones by a variety of techniques, both manual and automated, including affinity purification ('panning'), or by fluorescence activated cell sorting (FACS). Nishikawa et al (1998, Development vol 125, p 1747-1757) used cell surface markers recognised by antibodies to follow the differentiation of totipotent murine ES cells. Using FACS they were able to identify and purify cells of the haematopoletic lineage at various stages in their differentiation.

An alternative or complementary technique for enriching cell units of a particular genotype or phenotype is to genetically select the desired groups. This can be achieved for instance by introducing a selectable marker into the cell units, and to assay for viability under selective conditions, for instance see Soria et al (2000, Diabetes vol 49, p 1-6) who used such a system to select insulin secreting cells from differentiated ES cells. Li et al (1998, Curr Biol vol 8, p 971-974) identified neural progenitors by integrating the bifunctional selection marker/reporter βgeo (which provides for β-galactosidase activity and G418 resistance) into the Sox2 locus by homologous recombination in murine ES cells. Since one of the characteristics of neural progenitors is expression of Sox2, and therefore the integrated marker genes, these cells could be selected from non-neuronal lineages by addition of G418 after inducing differentiation using retinoic acid. Cell viability could be determined by inspection under a microscope, or by monitoring β-gal activity. Unlike phenotype-based selection approaches, which can be limited by the availability of an appropriate ligand or antibody, genetic selection can be applied to any differentially expressed gene.

Determination of the Identity or Cell Culture History of a Cell Unit

When handling large numbers of cell units, their identity and/or cell culture history (for example the chronology and the exact nature of a series of culture conditions that any one group or unit may have been exposed to) can become confused. For instance, the split-pool protocol of cell culture necessarily involves mixing cell units in each round, making it difficult to follow individual units. Determining the cell culture history of a cell unit in a mixture of cell units which have been subjected to multiple culture conditions is sometimes referred to as 'deconvolution' of the cell culture history. One method of doing this is to label cell units and it is therefore advantageous to label the cell units. Labelling may be performed at the beginning of an experiment, or during each round of an experiment and may involve a unique label (which may or may not be modified in the course of an experiment) or a series of labels which comprise a unique aggregate. Similarly, reading of the label(s) may take place during each round or simply at the end of the experiment. Preferably, unique labels such as RFID labels are read during each round, whereas labels added serially at each round are read at the end of an experiment.

Labelling of cell units may be achieved by a variety of means, for instance labelling either the cells themselves, or any material to which the cells are attached or otherwise associated with. Any of the chemical and non-chemical methods used to encode synthetic combinatorial libraries can be adapted for this purpose and some of these are described in Methods in Enzymology Vol 267 (1996), 'Combinatorial Chemistry', John N. Abelson (Editor); Combinatorial Chemistry, Oxford University Press (2000), Hicham Fenniri (Editor); K. Braeckmans et al., 'Scanning the code', Modern Drug Discovery (February 2003); K. Braeckmans et al., 'Encoding microcarriers: Present and Future Technologies'; Nature Reviews Drug Discovery, vol. 1, p. 447-456 (2002) all of which are herein incorporated by reference. Some examples of labelling methods follow.

One method of labelling cell units involves associating cell units with a tag that becomes sequentially modified as it is placed in different culture conditions. This may involve for instance the addition or subtraction of further units to the tag such that its stereochemistry, sequence or mass is altered; or the alteration of electronic memory as in read-write RF transponders (see below).

Another method of labelling cell units involves sequentially associating unique tags with the cell units whenever they are cultured under different conditions, such that subsequent detection and identification of the tags provides for an unambiguous record of the chronology and identity of the cell culture conditions to which the cell unit has been exposed. Tags can be taken up by cells, or attached to the cell surface by adsorption, or a suitable ligand or antibody, or conjugated to a cell-associated matrix such as a carrier by adsorption, colloidal forces or a variety of linkages such as covalent linkage or non-covalent linkage, e.g. biotin-streptavidin linkage. For instance, one simple tag that can be introduced to cells or attached to a matrix associated with cells is an oligonucleotide of defined length and/or sequence. Oligonucleotides may comprise any class of nucleic acid (e.g. RNA, DNA, PNA, linear, circular or viral) and may contain specific sequences for amplification (e.g. primer sequences for PCR) or labels for detection (e.g. fluorophores or quenchers, or isotopic tags). The detection of these may be direct, for instance by sequencing the oligos or by hybridising them to complementary sequences (e.g. on an array or chip), or indirect as by monitoring an oligonucleotide-encoded gene product, or the interference of the nucleotide with a cellular activity (e.g. antisense inhibition of a particular gene). An advantageous method of amplifying nucleic acids is by rolling circle amplification (RCA; 2002, V. Demidov, *Expert Rev. Mol. Diagn.* 2(6), p. 89-95) where nucleic acid tags can comprise RCA templates, elongation primers, or struts that aid the circularization of minicircle templates).

Any molecular or macromolecular tag can be used so long as it can be detected, including peptide tags, coloured or fluorescent compounds, secondary amines, halocarbons, mixtures of stable isotopes etc. Tags may attach to cell units directly or via an intermediary, for instance an antibody raised against a component of the cell unit, or via an interacting pair such as biotin-steptavidin. In addition tags can be protected against degradation by the components of the cell culture, for example by chemical or other modification or by encapsulation. Encapsulation of tags can take place in many different media, for example in beads many types of which are available from suppliers such as Bangs Laboratories Inc. (Fishers Ind., USA), and encapsulation may be used to standardise tag dosage in addition to providing components for tag amplification and/or detection (for example by providing PCR primers for use with a DNA tag). A preferred method of labelling cell units employs fluorescent beads such as those manufactured by Luminex Corporation (Austin, Tex., USA). The Luminex system comprises polystyrene beads which may or may not be externally derivatised (e.g. with avidin or antibody) and are internally dyed with differing ratios of two spectrally distinct fluorophores, and a reader which is capable of characterising the spectral signature of each bead. A further preferred method employs beads such as those manufactured by Bangs Laboratories Inc. (Fishers Ind., USA). The Bangs system comprises bead sets which can be distinguished based on differing sizes (e.g. bead sets of 4.4 µm and 5.5 µm diameter). Beads within each set can be furthermore distinguished from each other based on differing fluorescence intensity owing to differential loading with a single fluorescent dye. It is possible to use many different dyes with different absorption or emission characteristics, which can be internally loaded or attached externally to carriers by a multiplicity of means. It is furthermore possible to use 'quantum dots' to obtain a very high number of different fluorescent labels which can be read conveniently.

Cell growth substrates such as those described in connection with forming cell units can be derivatised or coated with substances that facilitate tagging and do not interfere with cell growth. A preferred method of derivatising carriers is to modify them covalently or non-covalently with biotin, to which a tag can be attached via streptavidin or avidin. In general it will be important to use a tag that will not itself induce a cellular effect (i.e. an inert tag), and that can be distinguished from molecules present in cell units or the culture media, and that can be attached to its target and subsequently detected in the background of such molecules. To facilitate detection, it may be advantageous to selectively elute tags from cell units or to strip off the cells from cell units using selective conditions. More complicated molecular tagging strategies can also be envisaged, including the strategy of 'binary encoding' where information is recorded by a set of binary codes assigned to a set of molecular tags and their mixtures.

Detection of tags can be accomplished by a variety of methods familiar to those skilled in the art. Methods include mass spectrometry, nuclear magnetic resonance, sequencing, hybridisation, antigen detection, electrophoresis, spectroscopy, microscopy, image analysis, fluorescence detection, etc.

Of particular interest are labelling or encoding strategies in which labelling is carried out only once or where labelling and/or detection are non-physical and therefore non-invasive. Radiofrequency Identification (RFID) is an example of a system exhibiting these properties. RFID employs transponders (RF tags), antennae and readers. An RF tag is a small electronic circuit, usually encased in glass or plastic, which in its simplest form provides access to a unique identification code that may be 'read', without contact or line of sight, by suitable electronics. Tags may also store information generated by the user, again without contact or line of sight. A 'reader' is an electronic unit that transfers information to and from one or more tags (it should be noted that the term reader is used interchangeably to mean both a read only and read/write unit). The size and features of a reader may vary considerably, and it may operate in isolation, or be connected to a remote computer system. An antenna is used to transmit information from a reader to a tag, and to receive information sent by an RF tag. The size and format of an antenna will reflect the specific application, and may range from a small circular coil to large planar structures. An RFID system may operate in isolation, or be connected to a remote computer for more comprehensive interpretation and manipulation of identification and associated data derived from a tag. One RFID strategy used in combinatorial chemistry is described in Nicolaou et al (1995, Angew Chem Intl Ed Engl, vol. 34, p. 2289) and comprises: (i) a porous enclosure containing a synthesis substrate and the semiconductor tag; (ii) the solid phase synthesis resin; (iii) a glass-encased Single or Multiple Addressable Radiofrequency Tag semiconductor unit capable of receiving, storing and emitting radiofrequency signals. A similar device could be adapted to growing and following cell units simply by replacing the solid phase synthesis resin with tissue culture microcarriers or suitable cell units. More variations of this can be envisaged including but not limited to (coated or uncoated) RF tags on which cells are grown directly, or RF tags implanted into cell units or organisms.

Thus tags do not necessarily have to be distinguished by their chemical or molecular structure in the first instance. Multiple variations of the non-chemical tagging strategy can be devised to determine the identity of a given cell unit in a mixture or of deducing the identity of the different cell units that comprise a mixture. For instance optical or visual methods of tagging have been described where different shaped objects, graphically encoded objects or different colours denote the identity of a sample (for example see 1998, Guiles et al, Angew. Chem. Intl Ed Engl, vol. 37, p 926; Luminex Corp, Austin Tex., USA; BD Biosciences; Memobead Technologies, Ghent, Belgium), or where a pattern or bar code is etched onto a substrate such as a ceramic bar and recognised using pattern recognition technology (for example see 1997, Xiao et al, Angew. Chem. Intl Ed Engl, vol 36, p 780; Smart-Bead Technologies, Babraham, UK).

A further method of tracking or labelling cell units is to encode their identity spatially, i.e. by their position in space. In this method different cell units are segregated in defined relative positions, and these positions denote or encode the identity of the units. For instance, cell units may be cultured in an array, whereby the identity and/or culture history of each unit is known and is associated to a particular position in the array. In their simplest forms such arrays can comprise collections of tissue culture flasks, wells of a multi-well plate, or locations on a glass slide or other surface. Examples of positional encoding strategies can be found in Geysen et al. (1984, Proc Natl Acad Sci USA vol. 81, p. 3998-4002), Fodor et al. (1991, Science vol. 251, p. 767-773), Ziauddin and Sabatini (2001, Nature, Vol. 411, p. 107-110), and Wu et al. (2002, Trends Cell Biol. Vol. 12(10), p. 485-8).

The invention has many facets, each of which may have many forms that may be combined to form numerous permutations of the invention. It will be apparent that it is not necessary to label all of the cell units in order to be able to deduce information about the outcomes resultant from a combination of cell culture protocols. Thus without labelling of cell units it would still be possible to assay large combinations of cell culture conditions according to the invention, and to determine whether one or more of these was capable of resulting in a particular cellular effect. However, cell units are preferably labelled. Labelling of a cell unit allows the derivation of useful information from the experiment regarding the outcome of the particular conditions sampled by the labelled cell unit, as opposed to all the cell units. Alternatively it is sometimes advantageous to label one or a few group(s) of cell units which have all been exposed to a certain culture protocol, for instance a group of cell units which have been segregated into the same medium during a particular split or pool step. It will also be apparent that labelling certain cell units allows one to infer the identity of other (perhaps unlabelled) cell units.

Similarly, it will be clear that performing cell culture experiments in which various conditions are omitted can give information regarding the utility of those conditions with respect to a particular experimental outcome. It would therefore be possible to evaluate each of the conditions sampled in a manner according to the invention by repeating the experiment a number of times, each time omitting a different set of conditions.

Split-split cell culture steps can also be used to determine the effect of a particular set of conditions on experimental outcome. In effect split-split steps result in the formation of particular lineages of cell units which have each been exposed to a unique cell culture conditions at the time of branching. By studying the different lineages it is possible to determine the utility of the tissue culture conditions studied at the branching point (FIG. 6), with respect to a particular experimental outcome.

The invention is further described in the following examples.

EXAMPLES

Example 1

Differentiation of ES Cell Units Using Split-Pool Cell Culture

A split-pool culture experiment was performed in order to assay tissue culture conditions that might give rise to neurons of a dopaminergic phenotype using a starter culture of undifferentiated mouse ES cells.

Undifferentiated ES cells were grown on gelatin-coated tissue culture plates in the presence of 1,400 U ml–1 of leukemia inhibitory factor (LIF; Chemicon) in ES cell medium consisting of knockout Dulbecco's minimal essential medium (DMEM; GIBCO/BRL) supplemented with 15% FCS, 100 mM MEM nonessential amino acids, 0.55 mM 2-mercaptoethanol, L-glutamine, and antibiotics (all from GIBCO/BRL). To induce embryoid body (EB) formation the cells were dissociated into a single-cell suspension by 0.05% trypsin and 0.04% EDTA in PBS and plated onto nonadherent bacterial culture dishes at a density of $2-2.5 \times 10^4$ cells cm$^{-2}$ in the medium described above. The EBs were formed for four days and then plated onto adhesive tissue culture surface in the ES cell medium. After 24 h of culture, selection of nestin-positive cells was accomplished by replacing the ES cell medium by serum-free Insulin/Transferrin/Selenium/Fibronectin (ITSFn) medium and incubating for 10 days.

These nestin-positive cells were used as the starting material for a split-pool culture experiment. Specifically, the cells were dissociated by 0.05% trypsin/0.04% EDTA, and seeded on >10,000 glass biospheres (Whatman, UK) at approximately $1.5-2 \times 10^5$ cells cm$^{-2}$. Tissue culture dishes used henceforth were made from non-adherent material. Sterile glass beads were pre-coated using polyomithine (15 mg ml$^{-1}$) and laminin (1 μg ml$^{-1}$, both from Becton Dickinson Labware, Bedford, Mass.). The beads were divided randomly into four sets, each of which was incubated in one of four tissue culture media (denoted A1, A2, A3 or A4) whose composition is given in Table 1 below. These are based on N2 medium modified according to Johe et al. (1996, Genes Dev, vol 10, p 3129-3140) and which is henceforth referred to simply as N2 medium.

TABLE 1

| | |
|---|---|
| A1 | N2 medium supplemented with 1 μg ml$^{-1}$ of laminin. |
| A2 | N2 medium supplemented with 1 μg ml$^{-1}$ of laminin, 10 ng ml$^{-1}$ of bFGF (R&D Systems, Minneapolis, MN). |
| A3 | N2 medium supplemented with 1 μg ml$^{-1}$ of laminin, 10 ng ml$^{-1}$ of bFGF (R&D Systems, Minneapolis, MN), murine N-terminal fragment of SHH (500 ng ml − 1, from R&D Systems). |
| A4 | N2 medium supplemented with 1 μg ml$^{-1}$ of laminin, 10 ng ml$^{-1}$ of bFGF (R&D Systems, Minneapolis, MN), murine N-terminal fragment of SHH (500 ng ml − 1, R&D Systems) and murine FGF8 isoform b (100 ng ml$^{-1}$, R&D Systems). |

The four sets of beads were exposed to the respective tissue culture media for two days and then beads from all four cultures were pooled, washed briefly in N2 medium, and again split into four sets each of which was incubated in one of media A1-A4. After two days this procedure was repeated again, in order to sample cell culture in various combinations of media A1-A4 over a six day period. After this time, beads from all four cultures were pooled, washed briefly in N2 medium, and randomly split into four new sets each of which was incubated in one of four new media (denoted B1, B2, B3 or B4) whose composition is given in Table 2 below.

TABLE 2

- B1 N2 medium supplemented with 1 µg ml$^{-1}$ of laminin, 10 ng ml$^{-1}$ of bFGF (R&D Systems, Minneapolis, MN), murine N-terminal fragment of SHH (500 ng ml$^{-1}$, R&D Systems) and murine FGF8 isoform b (100 ng ml$^{-1}$, R&D Systems).
- B2 N3FL medium: DMEM/F12 (1:1) medium containing insulin (25 µg/ml), transferrin (50 µg/ml), progesterone (20 nM), putrescine (100 µM), selenium chloride (30 nM), bFGF (5 ng/ml) and laminin (1 µg/ml),
- B3 N2 medium supplemented with 25 mM HEPES (pH 7.4), laminin (1 mg ml$^{-1}$), cAMP (1 µM, Sigma, St. Louis, MO) and ascorbic acid (200 µM, Sigma, St. Louis, MO).
- B4 N2 medium supplemented with laminin (1 mg ml$^{-1}$), cAMP (1 µM, Sigma, St. Louis, MO) and ascorbic acid (200 µM, Sigma, St. Louis, MO).

Each round of culture was for five days, then beads from all four cultures were pooled, washed briefly in N2 medium, and split into four sets each of which was again incubated in one of media B1-B4. This procedure was carried out a total of three times, such that the beads were present in the B media a total of 15 days.

Included in the composition of the different culture media was a unique oligonucleotide label that adhered to the glass microcarriers (or cells) in small quantities and was subsequently amplified and analysed in order to deduce the whereabouts of a microcarrier bead at any time in the split pool culture regimen. The DNA sequence of each label differed so as to distinguish between the different media (i.e. medium A1 vs medium A2) and also exposure to the same medium on two different rounds of split pool culture (i.e. medium A1 used on Day 0 vs on day 4). A summary of the split pool culture regimen in the various media over a total of 21 days is given in Table 3 below. Each entry in the table also shows (in parentheses) the identity of the label included in the tissue culture flask. The full DNA sequence of the label is shown in Table 4.

TABLE 3

| Day 0 | Day 2 | Day 4 | Day 6 | Day 11 | Day 16 |
|---|---|---|---|---|---|
| A1 (L1) | A1 (L5) | A1 (L9) | B1 (L13) | B1 (L17) | B1 (L21) |
| A2 (L2) | A2 (L6) | A2 (L10) | B2 (L14) | B2 (L18) | B2 (L22) |
| A3 (L3) | A3 (L7) | A3 (L11) | B3 (L15) | B3 (L19) | B3 (L23) |
| A4 (L4) | A4 (L8) | A4 (L12) | B4 (L16) | B4 (L20) | B4 (L24) |

TABLE 4

(SEQ ID NO.: 1)
L1 TGCAGGAATTCGCGCTATGCTaACGTGAAGcCACGTCGCCgCCGCC GCCGACCCGGCCGAATTCCTG (SEQ ID NO.: 2)
L2 TGCAGGAATTCGCGCTATGCTgACGTGAAGtCACGTCGCCaCCGCC GCCGACCCGGCCGAATTCCTG (SEQ ID NO.: 3)
L3 TGCAGGAATTCGCGCTATGCTcACGTGAAGaCACGTCGCCtCCGCC GCCGACCCGGCCGAATTCCTG

TABLE 4-continued (SEQ ID NO.: 4)
L4 TGCAGGAATTCGCGCTATGCTtACGTGAAGgCACGTCGCCcCCGCC GCCGACCCGGCCGAATTCCTG (SEQ ID NO.: 5)
L5 TGCAGGAATTCGCGCTATGCTAaCGTGAAGAcACGTCGCCAgCGCC GCCGACCCGGCCGAATTCCTG (SEQ ID NO.: 6)
L6 TGCAGGAATTCGCGCTATGCTAgCGTGAAGAtACGTCGCCAaCGCC GCCGACCCGGCCGAATTCCTG (SEQ ID NO.: 7)
L7 TGCAGGAATTCGCGCTATGCTAcCGTGAAGAaACGTCGCCAtCGCC GCCGACCCGGCCGAATTCCTG (SEQ ID NO.: 8)
L8 TGCAGGAATTCGCGCTATGCTAtCGTGAAGAgACGTCGCCAcCGCC GCCGACCCGGCCGAATTCCTG (SEQ ID NO.: 9)
L9 TGCAGGAATTCGCGCTATGCTAAaGTGAAGACcCGTCGCCACgGCC GCCGACCCGGCCGAATTCCTG (SEQ ID NO.: 10)
L10 TGCAGGAATTCGCGCTATGCTAAgGTGAAGACtCGTCGCCACaGCC GCCGACCCGGCCGAATTCCTG (SEQ ID NO.: 11)
L11 TGCAGGAATTCGCGCTATGCTAAcGTGAAGACaCGTCGCCACtGCC GCCGACCCGGCCGAATTCCTG (SEQ ID NO.: 12)
L12 TGCAGGAATTCGCGCTATGCTAAtGTGAAGACgCGTCGCCACcGCC GCCGACCCGGCCGAATTCCTG (SEQ ID NO.: 13)
L13 TGCAGGAATTCGCGCTATGCTAACaTGAAGACAcGTCGCCACCgCC GCCGACCCGGCCGAATTCCTG (SEQ ID NO.: 14)
L14 TGCAGGAATTCGCGCTATGCTAACgTGAAGACAtGTCGCCACCaCC GCCGACCCGGCCGAATTCCTG (SEQ ID NO.: 15)
L15 TGCAGGAATTCGCGCTATGCTAACcTGAAGACAaGTCGCCACCtCC GCCGACCCGGCCGAATTCCTG (SEQ ID NO.: 16)
L16 TGCAGGAATTCGCGCTATGCTAACtTGAAGACAgGTCGCCACCcCC GCCGACCCGGCCGAATTCCTG (SEQ ID NO.: 17)
L17 TGCAGGAATTCGCGCTATGCTAACGaGAAGCACcTCGCCACCGgC GCCGACCCGGCCGAATTCCTG (SEQ ID NO.: 18)
L18 TGCAGGAATTCGCGCTATGCTAACGgGAAGCACtTCGCCACCGaC GCCGACCCGGCCGAATTCCTG (SEQ ID NO.: 19)
L19 TGCAGGAATTCGCGCTATGCTAACGcGAAGCACaTCGCCACCGtC GCCGACCCGGCCGAATTCCTG (SEQ ID NO.: 20)
L20 TGCAGGAATTCGCGCTATGCTAACGtGAAGCACgTCGCCACCGcC GCCGACCCGGCCGAATTCCTG (SEQ ID NO.: 21)
L21 TGCAGGAATTCGCGCTATGCTAACGTaAAGACACGcCGCCACCGCg GCCGACCCGGCCGAATTCCTG (SEQ ID NO.: 22)
L22 TGCAGGAATTCGCGCTATGCTAACGTgAAGCACGtCGCCACCGCa GCCGACCCGGCCGAATTCCTG (SEQ ID NO.: 23)
L23 TGCAGGAATTCGCGCTATGCTAACGTcAAGACACGaCGCCACCGCt GCCGACCCGGCCGAATTCCTG TABLE 4-continued (SEQ ID NO.: 24)
L24 TGCAGGAATTCGCGCTATGCTAACGTtAAGACACGgCGCCACCGCc
GCCGACCCGGCCGAATTCCTG By split-pool culturing the stem cells three times in the different A media followed by three times in the different B media it was possible to sample 4096 different tissue culture protocols—this being the total number of different combinations of the above buffers to which different beads were exposed.

Following the final round of split pool culture the beads were pooled, washed briefly in N2 medium, and analysed by FACS using standard protocols. Briefly, cells were fixed in 4% paraformaldehyde/0.15% picric acid in PBS. In order to detect dopaminergic neurons, cells were stained using an anti-tyrosine hydroxylase monoclonal (Sigma) followed by a fluorescently labelled secondary antibody (Jackson Immunoresearch Laboratories, West Grove, Pa.) both according to the manufacturer's instructions.

The five beads with the highest fluorescence intensity were sorted into separate wells of a PCR plate and the oligonucleotide labels were amplified by thirty cycles of PCR using Taq polymerase (Stratagene, La Jolla, Calif.) and the primers shown in Table 5 below.

TABLE 5

| PRF1 | TGCAGGAATTCGCGCTATGC | (SEQ ID NO.: 25) |
|---|---|---|
| PRR2 | CAGGAATTCGGCCGGGTCGG | (SEQ ID NO.: 26) |

The PCR products were purified by phenol/chloroform extraction followed by ethanol precipitation, digested using the restriction enzyme EcoRI (New England Biolabs, Beverley, Mass.) and cloned into similarly prepared pBluescript II KS+ vector (Stratagene, La Jolla, Calif.). The recombinant vector was electroporated into competent *E. coli* DH5α and plated on medium containing ampicillin antibiotic. Two hundred colonies were picked for each bead analysed and plasmid DNA prepared and sequenced in the region of the polylinker.

The sequencing analysis revealed that the majority of beads carrying cells with a dopaminergic phenotype were labeled by oligos (L4, L8, L12, L16, L20 and L24). Correlating these labels to their respective cell culture conditions suggested that these beads had been partitioned in medium A1 over a total of six days (on Day 0, Day 2 and Day 4) followed by medium B4 for a further fifteen days (on Day 6, Day 11 and Day 16). It was deduced that this culture protocol was one appropriate for the production of dopaminergic neurons by processing mouse ES cells as described above.

Once these conditions were established, undifferentiated ES cells were again cultured according to the above protocol (i.e expansion, EB formation, nestin selection etc.) but without undergoing the process of split pool culture. Cells were grown on adhesive tissue culture plates instead of beads, oligonucleotide labels were not added to the different culture media, and only the successful culturing conditions were assayed. In this way larger numbers of dopaminergic cells could be produced and tested for patterns of gene expression. Total RNA was removed from cells obtained from four stages of the culture protocol: (1) pluripotent ES cell population; (2) embryoid bodies; (3) dissociated and plated cells undergoing selection for nestin; and (4) nestin positive cells cultured in buffer A4. cDNA was prepared using reverse transcriptase and priming with random hexamers and the amount of actin transcript normalised between the various samples. Neural cDNAs were prepared using the primers shown in Table 6:

TABLE 6

| GENE | FORWARD PRIMER | REVERSE PRIMER | +ve STAGE |
|---|---|---|---|
| Otx2 | CCATGACCTATA CTCAGGCTTCAGG (SEQ ID NO.: 27) | GAAGCTCCATATCC-C TGGGTGGAAAG (SEQ ID NO.: 28) | 1, (2, 3), 4 |
| Pax2 | CCAAAGTGGTGAC AAGATTGCC (SEQ ID NO.: 29) | GGGATAGGAAGGACGC TCAAAGAC (SEQ ID NO.: 30) | 3, 4 |
| Pax5 | CAGATGTAGTCCG C-CAAAGGATAG (SEQ ID NO.: 31) | ATGCCACTGATGGAGT ATGAGGAGCC (SEQ ID NO.: 32) | 3, 4 |
| En1 | TCAAGACTGACTCA CAGCAACCCC (SEQ ID NO.: 33) | CTTTGTCCTGAACCGT GGTGGTAG (SEQ ID NO.: 34) | 4 |
| Wnt1 | ACCTGTTGACGGAT TCCAAG (SEQ ID NO.: 35) | TCATGAGGAAGCGTAG GTCC (SEQ ID NO.: 36) | 3, 4 |
| Nurr1 | TGAAGAGAGCGGAG AAGGAGATC (SEQ ID NO.: 37) | TCTGGAGTTAAGAAAT CGGAGCTG (SEQ ID NO.: 38) | 3, 4 |
| nestin | GGAGTGTCGCTTAG AGGTGC (SEQ ID NO.: 39) | TCCAGAAAGCCAAGAG AAGC (SEQ ID NO.: 40) | (1), 3, 4 |

Table 6 also shows the stages in which transcripts of the various genes were detected by RT-PCR (parentheses indicate detection of traces). From these results it was deduced that expression of En1, Pa 2, Pax5, Wnt1 and Nurr1 would be a suitable marker for cells destined to a dopaminergic fate. Conversely, transfection of pluripotent stem cells with such genes, for example Nurr1, could result in commitment to a dopaminergic phenotype in vitro (Wagner et al, 1999, Nature Biotechnology, vol. 17, p 653-659).

Example 2

Split-Pool Cell Culture of HepG2 Cell Units

A split-pool culture experiment was performed in order to assay tissue culture conditions that might affect a particular cellular process, namely the expression and/or activity of cytochrome P450 (CyP450) metabolic enzymes. Members of this class of enzyme, such as 1A1 and 1A2, can be assayed with the use of a substrate, ethoxyresorufin, that is enzymatically hydrolyzed to produce a product, resorufin, that has distinct fluorescence characteristics that can be used to measure CyP450 enzyme activity. The expression of CyP450 enzymes can be regulated by inducer molecules, such as β-naphthoflavone, and inhibitors such as α-naphthoflavone, quinidine, or aminotriazole. It is also possible for some molecules to induce expression of a CyP450 gene(s), but inhibit activity of the enzyme product of that gene. Therefore, complicated patterns of expression and activity can arise according to the pattern of serial exposure of cells to regulatory compounds.

The human hepatoma cell line HepG2 was grown on CYTODEX 3 (Amersham Biosciences) in DME medium supplemented with L-glutamine, penicillin+streptomycin, and 10% heat-inactivated fetal calf serum. One day after seeding cell units were split into 5 groups and cultured in separate wells of a multiwell culture plate in culture medium containing 5 µM of one of α-naphthoflavone, β-naphthoflavone, quinidine, aminotriazole, or dimethylsulfoxide (DMSO; the solvent carrier for the test compounds). After 24 hours culture (37°, 5% $CO_2$), the cell units in the individual wells were washed twice with PBS, pooled together in growth medium, and split into five groups which were cultured in the five different media used in the first round. After a further 24 hours of culture the cell units were treated to a third round of split-pool culture as before. After a further 24 hours of culture, samples of beads were taken from the final five cell groups, and from a control group which had been cultured in standard medium with DMSO for the duration of the split-pool experiment.

For the CyP450 assay, aliquots of beads in growth medium were removed and the enzyme substrate ethoxyresorufin was added to a final concentration of 10 µM. The samples of beads were placed on a microscope slide with a cover slip, and observed immediately with an epifluorescent microscope using a standard filter set for Texas Red/rhodamine fluorescence (see FIG. 9). Control cells exhibited resorufin fluorescence about 15-20 minutes after addition of the substrate, and no fluorescence was detected in the absence of ethoxyresorufin. When cell units were treated with β-naphthoflavone in a control experiment, enzyme activity is evident within 5-10 minutes (data not shown). Cell units taken from the group which had undergone the split-pool culture procedure showed various degrees of enzyme activity (within 10 min) indicating that they had encountered a variety of conditions that induced or inhibited activity of the CyP450 enzymes capable of metabolizing ethoxyresorufin.

Example 3

Growth of Cell Units Comprising Pluripotent Stem Cells

Figure 7:
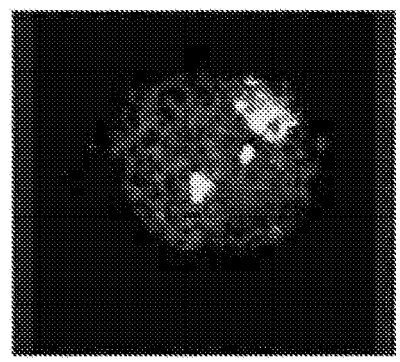
FIG. 7 shows cell units comprising pluripotent embryonic stem cells, expressing a chimeric Tau-Green Fluorescent Protein, attached to porous microcarriers CYTOPORE 2, Amersham Biosciences).
Figure 7:
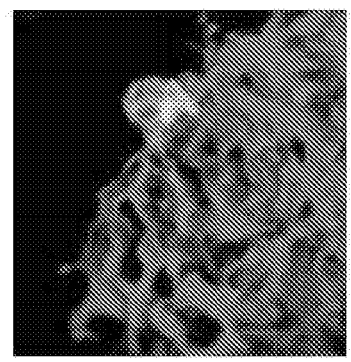

Pluripotent mouse ES cells expressing a Tau-GFP fusion protein were maintained on a feeder layer of mitomycin C-treated SNL cells (a STO cell derivative) in ES cell medium consisting of Iscove's medium supplemented with 15% FCS, 0.55 mM 2-mercaptoethanol, L-glutamine, antibiotics (all from GIBCO/BRL), and 1,400 U ml-1 of leukemia inhibitory factor (Chemicon) and split 1:5 every other day. ES cells and feeder cells used for the formation of cell units were transferred to a gelatin-coated flask and cultured for one day in ES medium to reduce the number of feeder cells in the culture. ES cells were trypsinised from the gelatin plates and washed with FCS medium, then incubated with either CYTOPORE 2 or CYTODEX 3 microcarriers (Amersham Biosciences) that had been hydrated in PBS, sterilised by autoclaving or 70% ethanol treatment, then washed with ES medium. The ES cells were seeded at a density of about 10 cells/microcarrier in a non-adherent plastic dish. The ES cell culture was maintained under standard conditions (5% $CO_2$, 37°), with replacement of half of the medium every other day with fresh ES medium (See FIG. 7). Growth of pluripotent cells was observed for five days under these conditions, after which the cells were transferred from ES cell medium to begin differentiation.

Example 4

Differentiation of Stem Cell Units by Split-Split Culture

Pluripotent mouse ES cell units were cultured for five days in ES cell medium (see example 3), the ES medium was decanted and the cell units washed twice with PBS to remove traces of ES medium. The bead population was split into three groups, and the PBS decanted and replaced with one of (i) ES cell medium; (ii) Dulbecco's modified Eagle's medium (DMEM) with 10% fetal calf serum; or (iii) Chemically Defined Medium (CDM; Wiles M V, Johansson B M, 1999, Exp. Cell Res., vol 247, p. 241-8). After one hour culture under standard conditions, each of the three groups were split into three further groups, each of which was incubated in one of: (i) the medium in which the cell groups were cultured; the medium in which the cell groups were cultured including 1 µM LiCl; or (iii) the medium in which the cell groups were cultured including 1 µm retinoic acid (RA). Every other day half the medium was replaced with the respective fresh medium.

Example 5

Figure 8:
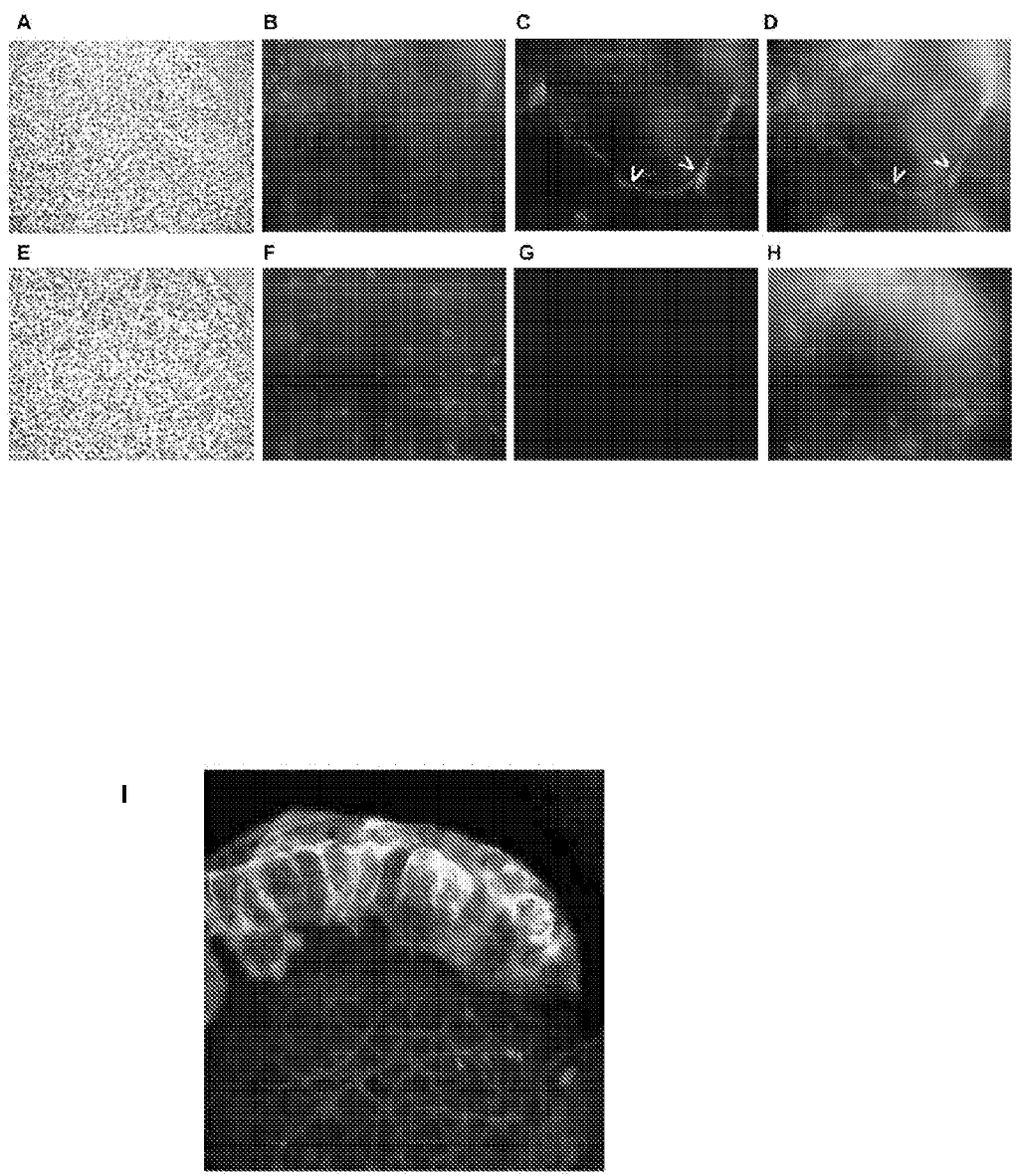
—FIG. 8 Panels A-H show cell units comprising ES cells expressing a Tau-Green Fluorescent Protein (GFP) fusion protein and the porous microcarrier CULTISPHER G undergoing differentiation as determined by antibody staining for expression of the glial marker GFAP. Panels A-D show a cell unit observed using a 40× objective under phase microscopy (A), and under fluorescence in which the cell nuclei are stained blue using DAPI (B), and the (red) markers GFAP (C) and (green) GFP (D) are apparent. Panels C and D show what appears to be a linear array of cells (white arrows) reminiscent of glia wrapping a neuronal process. Panels E-H show a control cell unit in which the primary anti-GFAP antibody had been omitted.

Detection of Cellular Processes Comprising Cellular Differentiation in Cell Units Using a Phenotypic Marker CULTISPHER G (Percell Biolytica) microcarriers were seeded with mouse ES cells expressing a Tau-GFP fusion protein and grown for four weeks in a serum-free medium (15% GIBCO KO serum replacement, Iscove's modified DMEM with GLUTAMAX (GIBCO), supplemented with penicillin/streptomycin and 1400 U/ml LIF). The medium was changed when the pH became acidic, as shown by the colour indicator in the medium. An aliquot of beads was removed and washed with PBS before fixation with 4% paraformaldehyde in PBS at 4° C. for 20 minutes. The beads were washed several times with PBS, resuspended in PBS/ 2.5% FCS, 0.1% Triton X-100, and split into two samples. One sample was made 1:200 with a murine anti-Glial Fibrillary Acidic Protein (GFAP) monoclonal antibody, and the other left as a control. After an overnight incubation at 4° C., the samples were washed 3 times with PBS, then both were incubated with a Cy3-labelled donkey anti-mouse antibody (Jackson ImmunoResearch) for 2 hours at room temperature. The samples were washed 3 times with PBS then spotted onto microscope slides with mounting medium containing DAPI (Vector). The majority of cells on the microcarriers exhibited specific staining for GFAP (see FIG. 8 A-H).

In a separate experiment cell units comprising mouse ES cells expressing a Tau-GFP fusion protein and CYTODEX 3 microcarriers (see Example 3), were transferred from ES medium to CDM and cultured for 4 days under standard conditions, after which the cell units were washed once with PBS and allowed to settle by gravity. The PBS was removed and the cell units fixed in 2% paraformaldehyde for 15 minutes at 4° C., after which the solution was removed and the cell units washed three times with PBS. The cell units were resuspended in PBS containing 2.5% fetal calf serum and 0.1% Triton X100 (Sigma) and split into three separate microfuge tubes. A mouse immunoglobulin specific for Tubulin beta III (Sigma) was added to one sample at a dilution of 1:200 and the antibody staining was allowed to proceed for 2 hours at room temperature with occasional resuspension. All three samples were then washed three times with a large excess of PBS. The sample incubated with the anti-tubulin antibodies and one other sample were then incubated for 2 hours at room temperature with a 1:200 dilution of a Cy3-conjugated donkey anti-mouse immunoglobulin (Jackson ImmunoResearch) in PBS/FCS/Triton X100. All three samples were then washed three times with a large excess of PBS, then the cell units were resuspended in mounting medium containing DAPI (Sigma), spotted onto microscope slides with cover slips, and viewed by epifluorescent or confocal microscopy (see FIG. 8, Panel I).

Example 6

Detection of Differential Gene Expression Owing to a Cellular Process

Cell units of mouse ES cells induced to differentiate by split-split culture (see example 4) were washed with PBS, and RNA prepared from the cell units using Rneasy reagents according to manufacturers instructions (Qiagen). RNA samples were then used to prepare first strand cDNA with oligo-dT priming using reverse transcriptase according to the manufacturer's instructions (Invitrogen). To normalize the concentrations of the samples, a 10-fold dilution series was made for each cDNA sample and subjected to 25, 30, and 35 rounds of polymerase chain reaction (PCR) with oligonucleotide primers for a 'housekeeping' gene, glyceraldehyde 3 phosphate dehydrogenase. Ethidium bromide staining of the resultant products separated on a 1.5% agarose gel was used to estimate the relative amount of cDNA in each sample. Equivalent amounts of cDNA from each sample were then used in a PCR reaction with DNA primers for Oct4 (predicted to occur in undifferentiated ES cells); Nestin (predicted to occur in differentiated neuronal progeny); or HNF3β (predicted to occur in differentiated endodermal progeny). The primer sequences were as follows:

| | | |
|---|---|---|
| HNF3b | ggacaagggaaatgagagg; | (SEQ ID NO.: 41) |
| | ataacacctcactccactacc | (SEQ ID NO.: 42) |
| Nestin | agtcagagcaagtgaatgg; | (SEQ ID NO.: 43) |
| | agaaacaagatctcagcagg | (SEQ ID NO.: 44) |
| Oct4 | cgcgttctctttggaaaggtgttc; | (SEQ ID NO.: 45) |
| | ctcgaaccacatccttctct | (SEQ ID NO.: 46) |
| G3PDH | accacagtccatgccatcac; | (SEQ ID NO.: 47) |
| | tccaccacctgttgctgta | (SEQ ID NO.: 48) |

The relative amounts of these distinguishing markers differed depending on the culture conditions to which the cell units were exposed. For example, RA in the ES medium induced expression of the endodermal marker HNF3β; while DMEM with RA, and to a lesser extent LiCl, led to expression of Nestin, a marker of neuronal precursors. The decrease in Oct4 was particularly marked in DMEM, although LiCl inhibited the reduction (see FIG. 11).

Example 7

Labelling of Cell Units Using RFID

Glass-encased ID 100-A transponders (Trovan) were treated for 2 hours with 1 N Hydrochloric acid, washed extensively with de-ionised water, then incubated for 2 hours with aminopropyltriethoxysilane (Sigma) in a glass vessel. The silane reagent was decanted and the tags washed serially with water, 70% ethanol, sterile deionized water, then phosphate-buffered saline. Tags were placed individually into wells of non-adherent bacterial plastic multi-well plates (Sterilin). A pluripotent line of ES cells expressing a Tau-GFP fusion transgene maintained in ES cell medium with LIF (Chemicon) on gelatin-coated plates were dissociated into a single-cell suspension by trypsin treatment. The cells were washed once with ES cell medium, resuspended in ES medium at $10^6$ cells/mL, and 250 μL of suspension was spotted onto each tag. After incubation of one hour under standard culture conditions (37°, 5% $CO_2$), 1.5 ml of additional ES medium was added and the plates returned to the incubator.

Transponders were also seeded with the human hepatoma cell line HepG2, and the mouse STO cell derivative, SNL. The pre-treatment and seeding process was performed as described for the ES cells, but the cells were maintained in DMEM with 10% FCS.

The adherent cultures were observed with a dissecting microscope, and fluorescently-tagged cells visualized using epifluorescence (see FIG. 10). The various cell types adhered, showed a normal spreading morphology, and proliferated on the transponders. The labeled cell units could be maintained for weeks with no obvious deterioration of the cell units or the labels. The unique identity of the cell units could be registered with a Trovan pocket reader without perturbing the cell culture conditions or the maintenance of the cell units.

Example 8

Labeling of Cell Units by Fluorescent, Molecular, or Optical Tags

CYTODEX 3 microcarriers (Amersham Biosciences) are composed of dextran with a surface layer of denatured collagen (gelatin). CYTODEX 3 beads (50 μl settled volume after hydration in PBS) were incubated 90 minutes at room temperature with an anti-collagen antibody conjugated to biotin (Abcam, Cambridge, UK), at a dilution of 1:50 in PBS with 2.5% fetal calf serum in a total volume of 200 μl. The beads were then washed three times in a large excess of PBS by resuspension then settling by gravity. A control sample was treated the same way, but without the addition of the anti-collagen antibody. The control and treated samples were each split into two, and one sample of each was incubated 30 minutes at room temperature with a streptavidin-FITC conjugate at a concentration of 2.5 μg/ml in a 250 μl volume of PBS/FCS. The remaining two samples were incubated under the same conditions, but without streptavidin-FITC. Beads pre-treated with the biotinylated anti-collagen antibody, followed by the streptavidin-FITC conjugate showed higher levels of fluorescence (see FIG. 12). Coating of microcarrier beads with a biotinylated antibody is a means to provide biotin moieties that in turn can bind readily detectable streptavidin conjugates. Since streptavidin can be conjugated to a very large number of molecular and macromolecular entities, it is thus possible to derivatise microcarrier beads such that they can bind with high affinity to a large range of tags.

In a separate experiment, CULTISPHER G (Percell Biolytica) microcarriers were labeled with latex beads which provide convenient tags. Microcarriers were hydrated in PBS, sterilised with 70% ethanol, washed with PBS, then covalently attached to biotin moieties. The biotinylation was performed using 10 mg biotinamidohexanoyl-6-aminohexanoic acid N-hydroxysuccinimide ester (Sigma) dissolved in 400 μl dimethylformamide, which was added to 1 ml settled volume of microcarriers in PBS. The reaction was allowed to proceed overnight at room temperature, and the microcarriers were washed 3 times with a large excess of PBS. An aliquot of treated beads and an unmodified control sample were incubated with $1 \times 10e5$ 1 μM diameter, streptavidin-coated red-fluorescent beads (Sigma), or with 2.5 μg/ml streptavidin-FITC (Sigma) in PBS with 2.5% foetal calf serum. The level of labelling with the bead tags (FIG. 12 E-H) or with FITC (FIG. 17 A-D) was compared using fluorescence microscopy In a further experiment, Cytodex 3 microcarriers were labeled with red or green fluorescent 1 μM diameter, streptavidin-coated beads (Sigma). Cytodex 3 microcarriers (Amersham Biosciences) were incubated with suspensions of red, green, or a 1:1 mixture of red and green latex beads for 30 minutes at room temperature in PBS with 2.5% FCS. The samples were washed three times in a large excess of PBS by resuspension then settling by gravity. An aliquot of the beads labeled by the red tags was then mixed with an aliquot of the same volume from the sample containing beads labeled by the green tags, to determine whether cross-labelling would occur. The samples were then viewed under an epifluorescence microscope using standard filter sets for detection of FITC and Texas Red/rhodamine (see FIGS. 13 and 14). Microcarriers could be robustly labeled using the latex bead tags, resulting in differently labeled populations. The admixture of the two populations resulted in no significant transfer of labels between microcarriers, meaning that the populations remained distinguishable. The microcarriers incubated with a combination of the two tags were stably labeled by both, indicating that a single microcarrier can be labeled with a multiplicity of tags. Since tags such as the ones used in this experiment can be conjugated to a very large number of reporters (e.g. different fluorophores, dyes, enzymes), it is possible to use these to label microcarriers with a large range of distinguishing tags. Additionally, it is possible to couple antibodies to the latex bead tags in order to direct them to microcarriers or cell units.

Example 9

Labeling of Cell Units by Fluorescent, Molecular, or Optical Tags

CYTODEX 3 microcarriers (Amersham) were seeded with ES cells expressing a Tau-GFP transgene. One day later, the microcarriers were washed with PBS, then incubated for 30 minutes at room temperature with a suspension of red, 1 μM diameter latex beads that were covalently linked to streptavidin (Sigma); and analysed immediately or after 24 hours post culture under standard conditions. Analysis involved washing three times in a large excess of PBS by resuspension then settling by gravity, and the samples were viewed under epifluorescence using standard filter sets for detection of FITC and Texas Red/rhodamine. Cell units comprising ES cells (green), and which had been labeled by colloidal interaction with latex bead tags (red) were apparent in each case.

Since beads composed of latex and other polymers can be conjugated to a very large number of molecular and supermolecular reporters, it is thus possible to label cell units with a large range of distinguishing labels.

Example 10

Manual Analysis and Isolation of Cell Units on the Basis of a Cellular Process

Cell units comprising mouse ES cells expressing a Tau-GFP fusion protein and CYTODEX 3 microcarriers were mixed with naked CYTODEX 3 microcarriers at a ratio of 1:100. The mixture was observed under a microscope using phase and fluorescence settings. Cell units expressing GFP were readily apparent when using fluorescence microscopy, even in a large excess of non-fluorescent carriers (see FIG. 15). Individual cell units could be sorted manually using a positioned mounted pipette to aspirate small volumes of the culture containing the cell units.

Example 11

Automated Analysis and Sorting of Labelled Microcarriers and Cell Units

It is desirable to be able to analyse and sort cell units which are labeled with various tags, or display particular cellular processes, in an automated or high throughput fashion. A COPAS Select instrument (Union Biometrica Inc., Somerville, Mass.) capable of sorting multicellular organisms and beads with diameter up to 0.5 mm was used to analyse cell units, microcarriers and labelled microcarriers. CYTODEX 3 (Amersham Bioosciences) were analysed by the instrument according to their size and optical characteristics (Time of Flight, TOF; Extinction, Ext), and exhibited a slight variation in size but no significant auto-fluorescence under the settings utilised (see FIG. 16 A/B). Labelling of CYTODEX 3 microcarriers with red streptavidin-conjugated latex beads (Sigma) (see Example 9) led to a detectable shift in red fluorescence (FIG. 16 C/D).

Cell units comprising CYTODEX 3 microcarriers seeded with ES cells expressing a Tau-GFP transgene were used in an experiment to sort cell units on the basis of cell number. Groups of cell units comprising cell units supporting various cell densities were passed through the instrument without fixation, and demonstrated a broad range of green fluorescence intensity (FIG. 16 E/F). The instrument was used to sort highly fluorescent cell units from cell units of low fluorescence. Samples subsequently analysed using epifluorescent microscopy revealed that cell units sorted on the basis of high fluorescence carried large numbers of live cells whereas cell units of low fluorescence were sparsely populated. Thus automated analysis, identification, and isolation of cell units can be performed according to multiple parameters, including cell number, phenotype, and labelling with identification tags.

Example 12

Identification of Tags from a Single Cell Unit

CULTISPHER G (Percell Biolytica) microcarriers were cross linked to biotin moieties (see Example 8) and the biotinylation confirmed by comparing the level of staining with streptavidin-FITC using fluorescence microscopy (FIG. 17 A-D).

Cell units were formed by the incubation of a single-cell suspension of $10^6$ TGFP ES cells with 250 μl settled volume biotinylated CULTISPHER G microcarriers in ES cell growth medium for 24 hours. A 50 μl sample of cell units was tagged with streptavidin-coated 1 μm red-fluorescent latex beads (Sigma) by incubating with approximately $5 \times 10^5$ tags for 15 minutes at room temperature. The cell units were washed free of excess latex beads by several rounds of resuspension and settling in large volumes of PBS. Epifluorescent microscopy was used to confirm that cell units were labelled by the latex bead tags (FIG. 17 E-G).

Cell units were placed in a petri dish mounted under a dissecting microscope, and individual units were isolated using a pipette and placed into 5 ml FACS tubes (Becton Dickinson Falcon). A 200 μl aliquot of a 1× solution of *Bacillus polymyxa* neutral protease (Dispase II, Roche) was added to each tube, and the microcarrier matrix was digested overnight at room temperature. The digest was run through a cytofluorimeter (Becton Dickinson FACScalibur) that had been calibrated to detect events in the 1 μm size range and in the far red (FL3) emission spectrum (FIG. 17 H, I). The identity of tags isolated from a single cell unit could be confirmed by detecting events which conform to the appropriate size and fluorescence criteria (FIG. 17 J, K).

Example 13

Identification of a Multiplicity of Tags Used to Label Cell Units

The availability of a large variety of latex beads of precise sizes and fluorescence characteristics allows for multiplex labelling of microcarriers. Biotinylated CULTISPHER G microcarriers (see Example 12) were labelled by serial incubation in media containing three different types of streptavidin-coated bead tags, differing in size, fluorescence emission spectrum and fluorescence intensity. The bead types used as tags were: 1) 1 μm green-fluorescent latex beads manufactured by Sigma; 2) bead set no. 1 in the series of 5.5 μm red-fluorescent latex beads (QUANTUMPLEX) manufactured by Bangs Laboratories; and 3) bead set no. 5 in the series of 4.4 μm red-fluorescent latex beads manufactured by Bangs Laboratories.

The tagged microcarriers were then proteolytically digested, and the liberated tags were subjected to FACS analysis as before (see Example 12). The cytofluorimeter (Becton Dickinson FACSCALIBUR) was calibrated with samples of the tags to set the size gates (FIG. 19 A), and the fluorescence signatures of the three different tags were detected by analysing events in the appropriate (green or red) fluorescence channels (FIG. 18 B-D).

The invention claimed is:

1. A method for determining the effect of a plurality of culture conditions on a cell, comprising the steps of:
   a) providing a first set of groups of cell units each comprising one or more cells, and exposing said groups to desired culture conditions, wherein cell units are labelled;
   (b) pooling two or more of said groups to form at least one second pool;
   (c) subdividing the second pool to create a further set of groups of cell units;
   (d) exposing said further groups to at least one change of culture conditions;
   (e) repeating steps (b)-(d) iteratively; and
   (f) assessing the effect on a given cell unit of the culture conditions to which it has been exposed, wherein the label(s) reflect(s) the culture conditions to which the cell unit has been exposed.

2. A method according to claim 1, wherein the label is spatially encoded.

3. A method according to claim 1, wherein the label is selected from the group consisting of an oligonucleotide, a peptide, a fluorescent compound, a secondary amine, a halocarbon, a mixture of stable isotopes, a bar code, an optical tag, a bead and a radiofrequency encoding tag and a quantum dot.

4. A method according to claim 1, wherein the cells are cultured in cell units, each cell unit comprising one or more cells.

5. A method according to claim 4, wherein the cell units are single cells.

6. A method according to claim 4, wherein each cell unit comprises one or more cells adherent to or bounded by a solid substrate.

7. A method according to claim 6, wherein the solid substrate is a microcarrier or bead.

8. A method according to claim 6, wherein the solid substrate is a well or medium-permeable barrier.

9. A method according to claim 1, wherein the culture conditions are media to which the cell is exposed.

10. A method according to claim 9, wherein the media contain one or more specific agents which influence a cellular process.

11. A method according to claim 1, wherein the cell culture conditions comprise culturing at one or more specific temperatures.

12. A method according to claim 1, wherein the cell culture conditions comprise culturing on one or more specific substrates.

* * * * *